(12) United States Patent
Takahashi

(10) Patent No.: US 8,280,000 B2
(45) Date of Patent: Oct. 2, 2012

(54) RADIATION PHASE CONTRAST IMAGING APPARATUS

(75) Inventor: Kenji Takahashi, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 350 days.

(21) Appl. No.: 12/662,642

(22) Filed: Apr. 27, 2010

(65) Prior Publication Data

US 2010/0272235 A1   Oct. 28, 2010

(30) Foreign Application Priority Data

Apr. 28, 2009   (JP) ................................. 2009-109811

(51) Int. Cl.
*G01N 23/04* (2006.01)
(52) U.S. Cl. ........................................................ 378/62
(58) Field of Classification Search ............ 378/19, 378/62, 36, 145, 146, 84, 85
See application file for complete search history.

(56) References Cited

U.S. PATENT DOCUMENTS

| | | | |
|---|---|---|---|
| 5,812,629 A | 9/1998 | Clauser | |
| 7,180,979 B2 | 2/2007 | Momose | |
| 2007/0183563 A1* | 8/2007 | Baumann et al. | ............... 378/19 |
| 2009/0092227 A1 | 4/2009 | David et al. | |

FOREIGN PATENT DOCUMENTS

| | | |
|---|---|---|
| JP | 2006-259264 | 9/2006 |
| JP | 2007-203062 | 8/2007 |
| JP | 2007-203063 | 8/2007 |
| JP | 2007-206075 | 8/2007 |

* cited by examiner

*Primary Examiner* — Irakli Kiknadze
(74) *Attorney, Agent, or Firm* — Jean C. Edwards, Esq.; Edwards Neils PLLC

(57) ABSTRACT

Providing a radiation emission unit that includes a radiation source and outputs a fan beam of radiation, a diffraction grating onto which radiation outputted from the radiation emission unit is emitted, and a periodic information imaging radiation image detector that includes multiple linear electrodes and detects periodic information of radiation diffracted by the diffraction grating, disposing the radiation emission unit and the periodic information imaging radiation image detector such that an extending direction of the linear electrodes of the periodic information imaging radiation image detector is perpendicular to a fan surface of the fan beam having a larger spread angle, and configuring the radiation emission unit to scan the fan beam in the perpendicular direction.

14 Claims, 21 Drawing Sheets

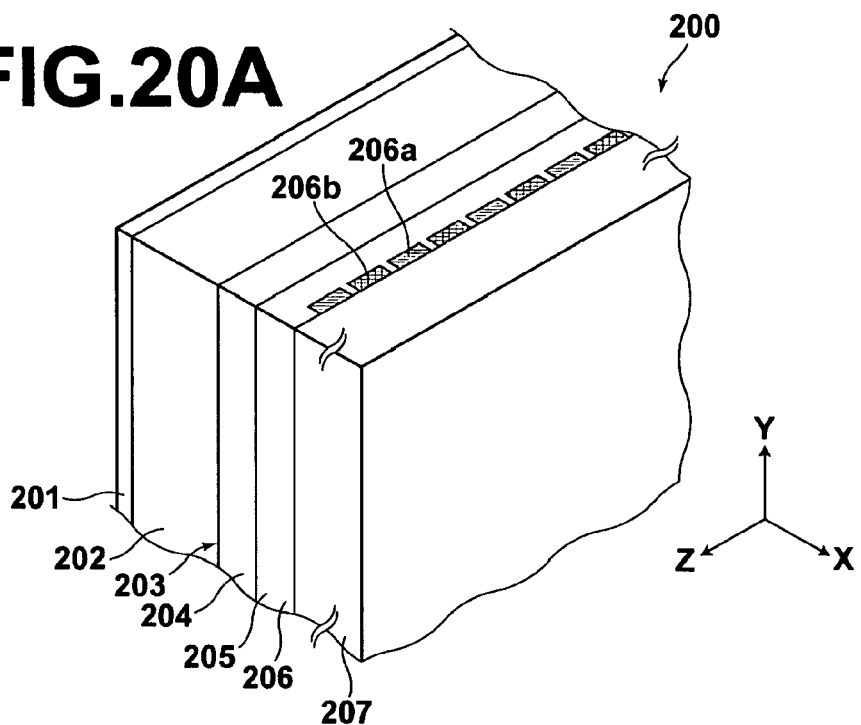
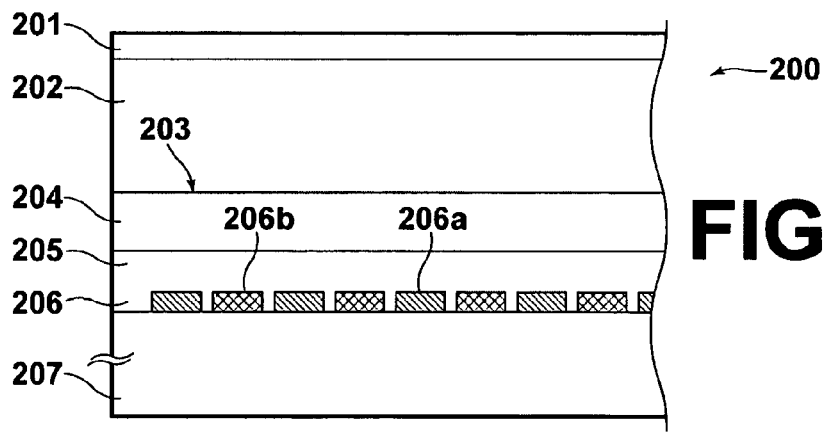
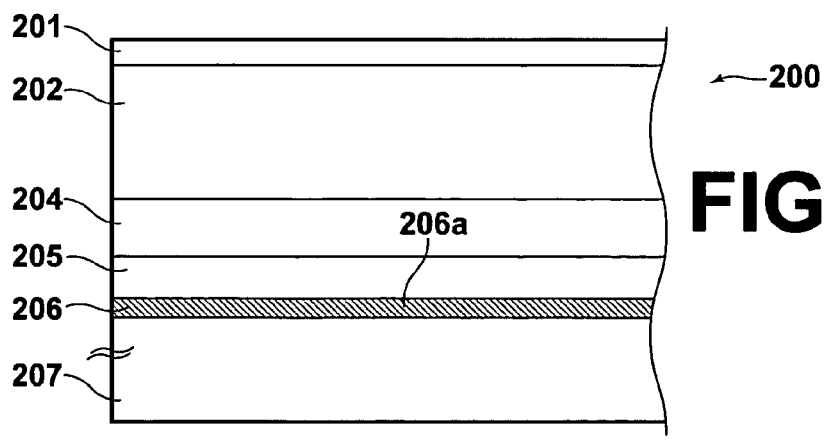

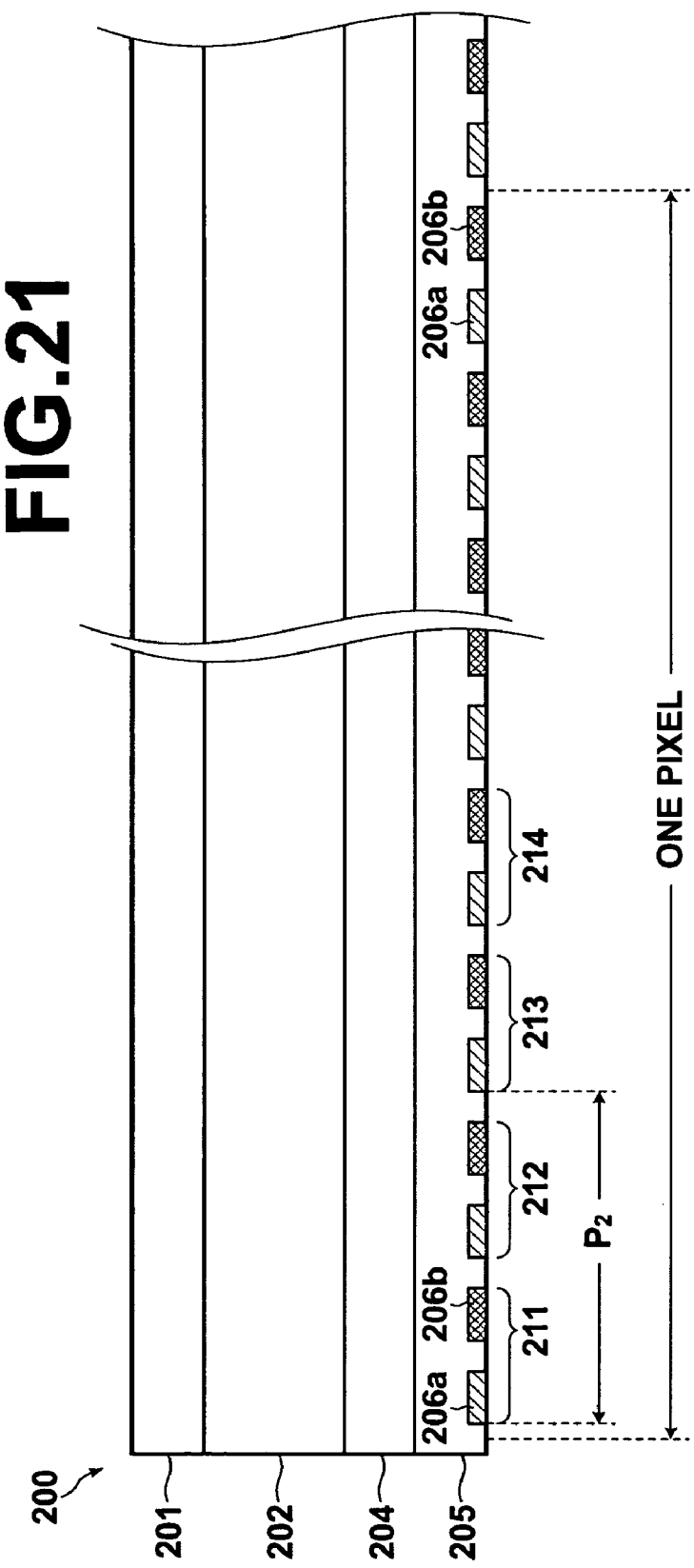

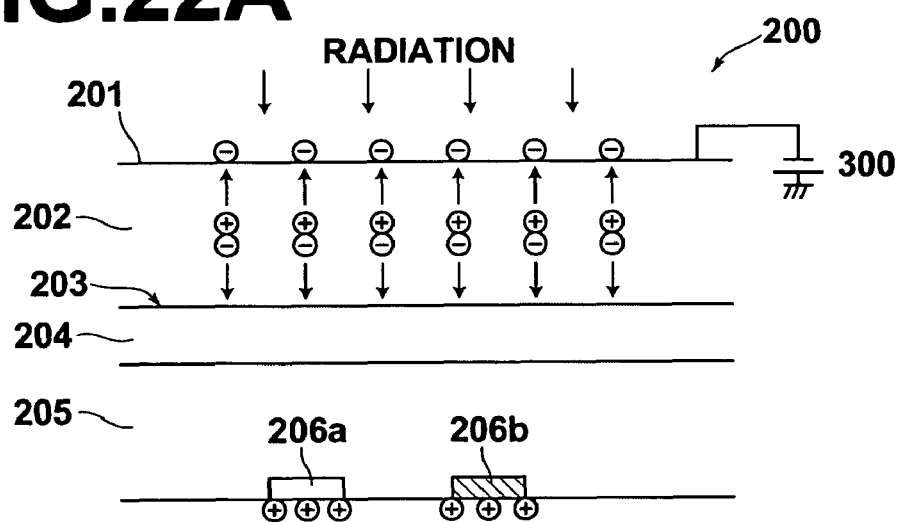
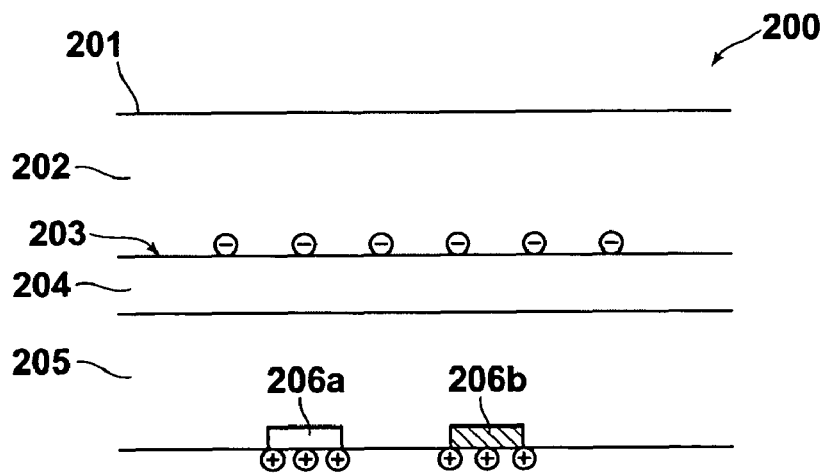

FIG.26
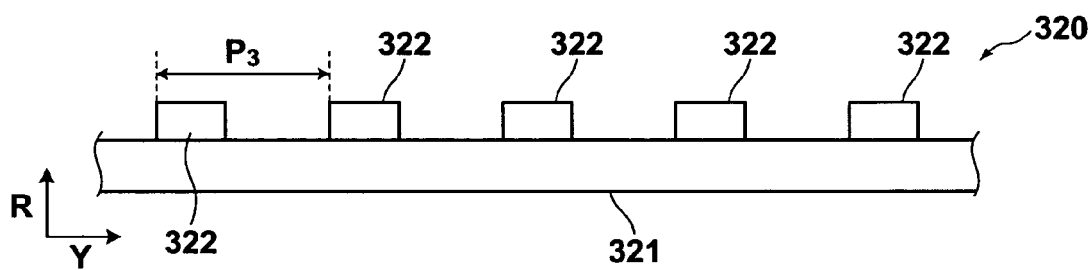
FIG.27
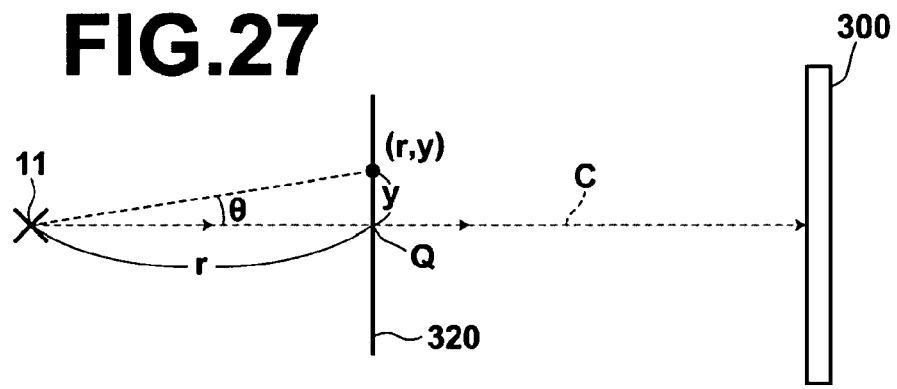
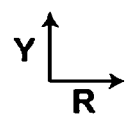

RADIATION PHASE CONTRAST IMAGING APPARATUS

CROSS-REFERENCE TO RELATED APPLICATIONS

The present application claims priority from Japanese Patent Application No. 2009-109811, filed Apr. 28, 2009, the contents of which are herein incorporated by reference in their entirety.

BACKGROUND OF THE INVENTION

1. Field of the Invention

The present invention relates to a radiation phase contrast imaging apparatus that employs a diffraction grating.

2. Description of the Related Art

An X-ray phase contrast imaging apparatus, which utilizes Talbot effect by a diffraction grating and Moire fringes in combination with another diffraction grating, i.e., X-ray Talbot interferometer has been studied as described, for example, in U.S. Pat. Nos. 5,812,629 and 7,180,979.

U.S. Pat. Nos. 5,812,629 and 7,180,979 propose X-ray imaging apparatuses that include an X-ray source, two diffraction gratings, and an X-ray image detector, and in each apparatus the two diffraction gratings and X-ray image detector are planar shaped.

For medical diagnostic applications, an X-ray source that radiates widely spreading beams is generally used. X-rays emitted by such an X-ray source can pass through the diffraction gratings at a center portion without any difficulty, but as X-ray incident on a portion other than the center portion, X-rays may be gradually absorbed and shielded by diffraction members. In this manner, It is difficult for X-rays emitted widely spread to pass through the diffraction gratings because the X-rays are incident from oblique directions. For example, Japanese Unexamined Patent Publication No. 2006-259264 proposes an amplitude modulation grating in which metal X-ray absorption members, each having a width of 2 to 10 µm and a thickness of 25 to 100 µm, are disposed at an equal interval of 2 to 10 µm. It can be thought that the use of such a diffraction grating may possibly cause the problem described above. Accordingly, large-size X-ray phase contrast imaging has been difficult to adopt practically in medical diagnostic applications.

Consequently, Japanese Unexamined Patent Publication No. 2007-206075 proposes an X-ray imaging apparatus structured such that a strip of the diffraction grating does not form a shadow in a beam path.

Japanese Unexamined Patent Publication No. 2007-203063 describes an X-ray imaging apparatus having a detection element formed of multiple vertically long detection strips parallel to the grating lines of the phase grating. The X-ray imaging apparatus like this may obtain a phase image by a single image acquisition and may reduce the number of image acquisition times. Japanese Unexamined Patent Publication No. 2007-203062 describes an X-ray imaging apparatus that obtains a phase contrast image in the same manner as in Japanese Unexamined Patent Publication No. 2007-203063 and includes scintillation strips.

Further, U.S. Patent Application Publication No. 20090092227 proposes a slot-scanning X-ray phase contrast imaging apparatus.

The X-ray imaging apparatuses described in Japanese Unexamined Patent Publication No. 2007-206075 and U.S. Patent Application Publication No. 20090092227 are apparatuses that obtain a phase contrast image using a fan beam or a cone beam, but there are various restrictions and preferable conditions in order to obtain a large-size view of X-ray phase image.

Where a detection element formed of multiple vertically long detection strips is provided as in Japanese Unexamined Patent Publication Nos. 2007-203063 and 2007-203062, it is possible to reduce the number of X-ray exposure times for obtaining a phase contrast image, but it is necessary to design the pitch between each detection strip much narrower. It is difficult to manufacture such narrower strips.

In view of the circumstances described above, it is an object of the present invention to provide a radiation phase contrast imaging apparatus capable of performing a large-size view of a radiation phase contrast imaging and being manufactured easily.

SUMMARY OF THE INVENTION

A radiation phase contrast imaging apparatus of the present invention is an apparatus, including:

a radiation emission unit that includes a radiation source and outputs a fan beam of radiation;

a diffraction grating onto which radiation outputted from the radiation emission unit is emitted; and a periodic information imaging radiation image detector that includes multiple linear electrodes and detects periodic information of radiation diffracted by the diffraction grating, wherein:

the radiation emission unit and the periodic information imaging radiation image detector are disposed such that an extending direction of the linear electrodes of the periodic information imaging radiation image detector is perpendicular to a fan surface of the fan beam having a larger spread angle; and the radiation emission unit is configured to scan the fan beam in the perpendicular direction.

In the radiation phase contrast imaging apparatus of the present invention described above, the periodic information imaging radiation image detector may be disposed along a cylindrical surface with a cylinder axis passing through the radiation source and parallel to the extending direction of the linear electrodes.

A radiation phase contrast imaging apparatus of the present invention is an apparatus, including:

a radiation emission unit that includes a radiation source and outputs a fan beam of radiation;

a diffraction grating onto which radiation outputted from the radiation emission unit is emitted; and a periodic information imaging radiation image detector that includes multiple linear electrodes and detects periodic information of radiation diffracted by the diffraction grating, wherein:

the radiation emission unit and the periodic information imaging radiation image detector are disposed such that an extending direction of the linear electrodes of the periodic information imaging radiation image detector is parallel to a fan surface of the fan beam having a larger spread angle; and the radiation emission unit is configured to scan the fan beam in a direction perpendicular to the fan surface.

In the radiation phase contrast imaging apparatus of the present invention described above, the periodic information imaging radiation image detector may be disposed on a planar surface or along a cylindrical surface with a cylinder axis passing through the radiation source and parallel to the direction the linear electrodes are arrayed.

Further, in the radiation phase contrast imaging apparatus of the present invention described above, the periodic information imaging radiation image detector may be configured to be shifted in the perpendicular direction according to the scanning of the fan beam.

Still further, the periodic information imaging radiation image detector may be configured to be shifted along an arc with a straight line connecting between the radiation source and the periodic information imaging radiation image detector as the radius.

A radiation phase contrast imaging apparatus of the present invention is an apparatus, including:

a radiation emission unit that includes a radiation source and outputs a fan beam of radiation;

a first diffraction grating onto which radiation outputted from the radiation emission unit is emitted;

a second diffraction grating that diffracts radiation diffracted by the first diffraction grating; and a radiation image detector that detects radiation diffracted by the second diffraction grating, wherein:

the radiation emission unit and the first and second diffraction gratings are disposed such that an extending direction of diffraction members of the first and second diffraction gratings is perpendicular to a fan surface of the fan beam having a larger spread angle;

the radiation emission unit is configured to scan the fan beam in the perpendicular direction; and the second diffraction grating is disposed along a cylindrical surface with a cylinder axis passing through the radiation source and parallel to the extending direction of the diffraction members.

In the radiation phase contrast imaging apparatus of the present invention described above, the second diffraction grating may be configured to be shifted in the perpendicular direction according to the scanning of the fan beam.

A radiation phase contrast imaging apparatus of the present invention is an apparatus, including:

a radiation emission unit that includes a radiation source and outputs a fan beam of radiation;

a first diffraction grating onto which radiation outputted from the radiation emission unit is emitted;

a second diffraction grating that diffracts radiation diffracted by the first diffraction grating; and a radiation image detector that detects radiation diffracted by the second diffraction grating, wherein:

the radiation emission unit and the first and second diffraction gratings are disposed such that an extending direction of diffraction members of the first and second diffraction gratings is perpendicular to a fan surface of the fan beam having a larger spread angle;

the radiation emission unit is configured to scan the fan beam in the perpendicular direction; and the second diffraction grating is configured to be shifted along an arc with a straight line connecting between the radiation source and the second diffraction grating as the radius.

A radiation phase contrast imaging apparatus of the present invention is an apparatus, including:

a radiation emission unit that includes a radiation source and outputs a fan beam of radiation;

a first diffraction grating onto which radiation outputted from the radiation emission unit is emitted;

a second diffraction grating that diffracts radiation diffracted by the first diffraction grating; and a radiation image detector that detects radiation diffracted by the second diffraction grating, wherein:

the radiation emission unit and the first and second diffraction gratings are disposed such that an extending direction of diffraction members of the first and second diffraction gratings is parallel to a fan surface of the fan beam having a larger spread angle;

the radiation emission unit is configured to scan the fan beam in a direction perpendicular to the fan surface; and the second diffraction grating is disposed on a planar surface or along a cylindrical surface with a cylinder axis passing through the radiation source and parallel to the direction the diffraction members are arrayed.

In the radiation phase contrast imaging apparatus of the present invention described above, the second diffraction grating may be configured to be shifted in the perpendicular direction according to the scanning of the fan beam.

A radiation phase contrast imaging apparatus of the present invention is an apparatus, including:

a radiation emission unit that includes a radiation source and outputs a fan beam of radiation;

a first diffraction grating onto which radiation outputted from the radiation emission unit is emitted;

a second diffraction grating that diffracts radiation diffracted by the first diffraction grating; and a radiation image detector that detects radiation diffracted by the second diffraction grating, wherein:

the radiation emission unit and the first and second diffraction gratings are disposed such that an extending direction of diffraction members of the first and second diffraction gratings is parallel to a fan surface of the fan beam having a larger spread angle;

the radiation emission unit is configured to scan the fan beam in the perpendicular direction; and the second diffraction grating is configured to be shifted along an arc with a straight line connecting between the radiation source and the second diffraction grating as the radius.

According to a radiation phase contrast imaging apparatus of an embodiment of the present invention, a periodic information imaging radiation image detector having multiple linear electrodes is used, so that the detector may be manufactured easily. Further, the radiation emission unit and the periodic information imaging radiation image detector are disposed such that an extending direction of the linear electrodes of the periodic information imaging radiation image detector is perpendicular or parallel to a fan surface of the fan beam having a larger spread angle and the radiation emission unit is configured to scan the fan beam in the perpendicular direction. This allows large size view of radiation phase imaging to be performed.

In radiation phase contrast imaging apparatus described above, when the periodic information imaging radiation image detector is disposed along a cylindrical surface with a cylinder axis passing through the radiation source and parallel to the extending direction of the linear electrodes, the blockage of radiation by the linear electrodes of the periodic information imaging radiation image detector may be avoided.

Further, in radiation phase contrast imaging apparatus described above, when the periodic information imaging radiation image detector is configured to be shifted in the perpendicular direction according to the scanning of the fan beam, the size of the periodic information imaging radiation image detector may be reduced, which allows easy manufacture and improved manufacturing yield, resulting in cost reduction.

Still further, if the periodic information imaging radiation image detector is configured to be shifted along an arc with a straight line connecting between the radiation source and the periodic information imaging radiation image detector as the radius, the blockage of radiation by the linear electrodes of the periodic information imaging radiation image detector may be avoided efficiently.

According to a radiation phase contrast imaging apparatus of an embodiment of the present invention, the radiation emission unit and the first and second diffraction gratings are disposed such that an extending direction of diffraction members of the first and second diffraction gratings is perpendicular to a fan surface of the fan beam having a larger spread angle, and the radiation emission unit is configured to scan the fan beam in the perpendicular direction. This allows large size view of radiation phase imaging to be performed. Further, the second diffraction grating is disposed along a cylindrical surface with a cylinder axis passing through the radiation source and parallel to the extending direction of the diffraction members, so that the blockage of radiation by the diffraction members of the second diffraction grating may be avoided.

According to a radiation phase contrast imaging apparatus of an embodiment of the present invention, the radiation emission unit and the first and second diffraction gratings are disposed such that an extending direction of diffraction members of the first and second diffraction gratings is perpendicular to a fan surface of the fan beam having a larger spread angle, and the radiation emission unit is configured to scan the fan beam in the perpendicular direction. This allows large size view of radiation phase imaging to be performed. Further, the second diffraction grating is configured to be shifted along an arc with a straight line connecting between the radiation source and the second diffraction grating as the radius, so that the blockage of radiation by the diffraction members of the second diffraction grating may be avoided.

According to a radiation phase contrast imaging apparatus of an embodiment of the present invention, the radiation emission unit and the first and second diffraction gratings are disposed such that an extending direction of diffraction members of the first and second diffraction gratings is parallel to a fan surface of the fan beam having a larger spread angle, and the radiation emission unit is configured to scan the fan beam in a direction perpendicular to the fan surface. This allows large size view of radiation phase imaging to be performed. Further, the second diffraction grating is disposed along a cylindrical surface with a cylinder axis passing through the radiation source and parallel to a direction the diffraction members are arrayed, so that the blockage of radiation by the diffraction members of the second diffraction grating may be avoided.

According to a radiation phase contrast imaging apparatus of an embodiment of the present invention, the radiation emission unit and the first and second diffraction gratings are disposed such that an extending direction of diffraction members of the first and second diffraction gratings is parallel to a fan surface of the fan beam having a larger spread angle, and the radiation emission unit is configured to scan the fan beam in the perpendicular direction. This allows large size radiation phase imaging to be performed. Further, the second diffraction grating is configured to be shifted along an arc with a straight line connecting between the radiation source and the second diffraction grating as the radius, so that the blockage of radiation by the diffraction members of the second diffraction grating may be avoided.

BRIEF DESCRIPTION OF THE DRAWINGS

FIG. 20A is a cross-sectional view of a periodic information imaging radiation image detector of the radiation phase contrast imaging apparatus according to a second embodiment, illustrating the schematic configuration thereof.

FIG. 20B is an XZ cross-sectional view of the periodic information imaging radiation image detector shown in FIG. 20A.

FIG. 20C is an XY cross-sectional view of the periodic information imaging radiation image detector shown in FIG. 20A.

FIG. 21 illustrates a structure of linear electrodes of periodic information imaging radiation image detector of the radiation phase contrast imaging apparatus according to the second embodiment of the present invention.

FIG. 22A, 22B illustrate a recording operation for recording a radiation image in the periodic information imaging radiation image detector of the second embodiment of the present invention.

FIG. 26 is a schematic configuration diagram of a diffraction grating.

FIG. 27 illustrates conditions of fan beam spread angle.

DESCRIPTION OF THE PREFERRED EMBODIMENTS

Figure 1:
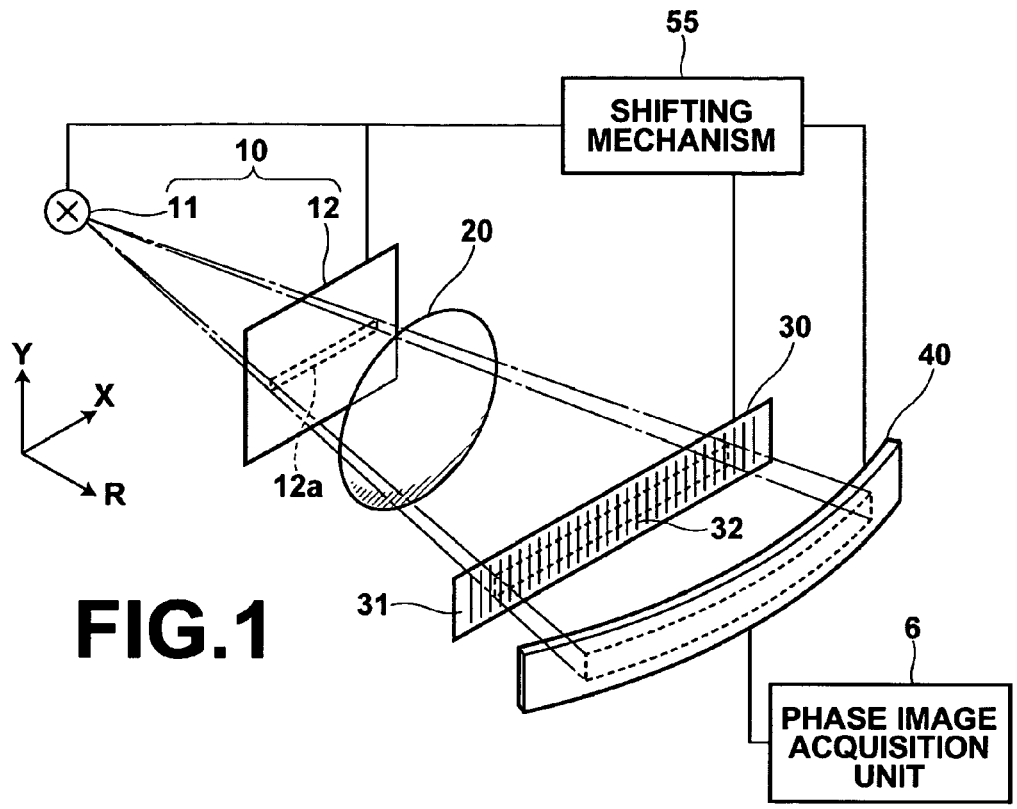
FIG. 1 is a schematic configuration diagram of a first embodiment of the radiation phase contrast imaging apparatus of the present invention.
Figure 2:
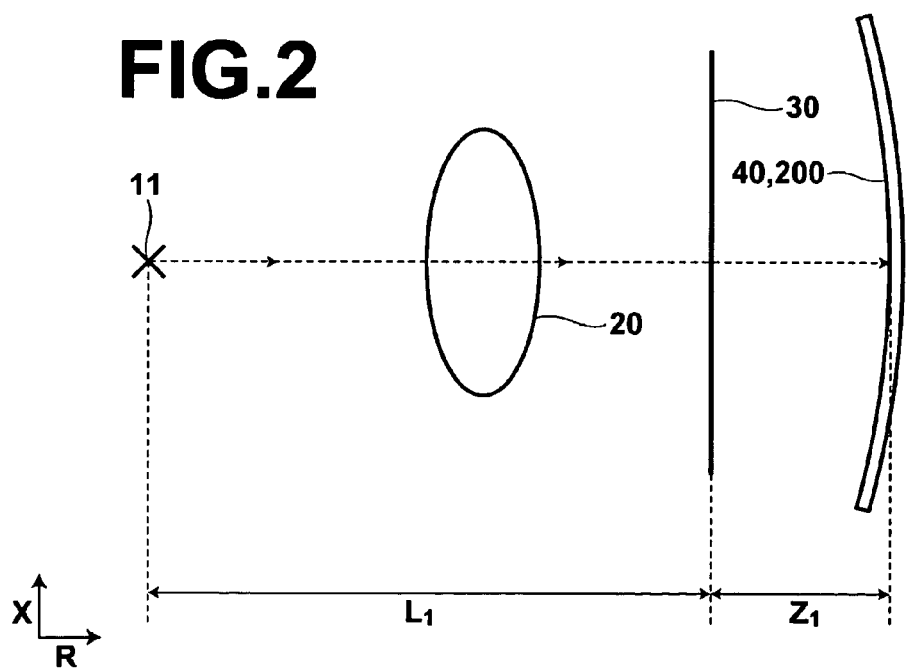
FIG. 2 is an X-R cross-sectional view of the radiation phase contrast imaging apparatus shown in FIG. 1.

Hereinafter, a first embodiment of the radiation phase contrast imaging apparatus of the present invention will be described with reference to the accompanying drawings. FIG. 1 is a perspective view of the radiation phase contrast imaging apparatus according to the first embodiment, illustrating the schematic configuration thereof. FIG. 2 is a top view (X-R cross-section) of the radiation phase contrast imaging apparatus shown in FIG. 1. The thickness direction in FIG. 2 corresponds to Y direction in FIG. 1.

As illustrated in FIG. 1, the radiation phase contrast imaging apparatus of the present embodiment includes radiation emission unit 10 for emitting radiation onto subject 20, diffraction grating 30 for receiving radiation transmitted through subject 20 and diffracting the radiation, periodic information imaging radiation image detector 40 for detecting periodic information of the radiation diffracted by diffraction grating 30, phase contrast image acquisition unit 6 for forming a phase image based on an image signal detected by periodic information imaging radiation image detector 40, and shifting mechanism 55 for shifting radiation source 11 and slit member 12 in radiation emission unit 10, diffraction grating 30, and periodic information imaging radiation image detector 40 along Y direction.

As shown in FIG. 1, radiation emission unit 10 includes radiation source 11 that emits radiation and slit member 12 that allows and restricts the passage of radiation emitted from radiation source 11 to output the radiation as a fan beam.

Slit member 12 is formed of a material that absorbs radiation and slit 12a is formed in the central portion thereof for passing radiation. Preferably, the size of slit 12a is such that the emission range of the fan beam in Y direction (smaller spread angle direction) on periodic information imaging radiation image detector 40 corresponds to a plurality of pixels of the detector.

As for radiation source 11, for example, a micro focus X-ray source, an X-ray source of a cold cathode electron source combined with a metal target and slits parallel to linear electrodes of periodic information imaging radiation image detector 40, an X-ray source of a cold cathode electron source combined with targets of metal wires parallel to linear electrodes of periodic information imaging radiation image detector 40, or an X-ray source of cold cathode electron sources parallel to linear electrodes of periodic information imaging radiation image detector 40 combined with metal targets may be used. Any of the radiation sources described above is formed as a radiation source related to Talbot interferometer, Talbot-Lau interferometer, or dark field X-ray phase contrast imaging.

Figure 3:
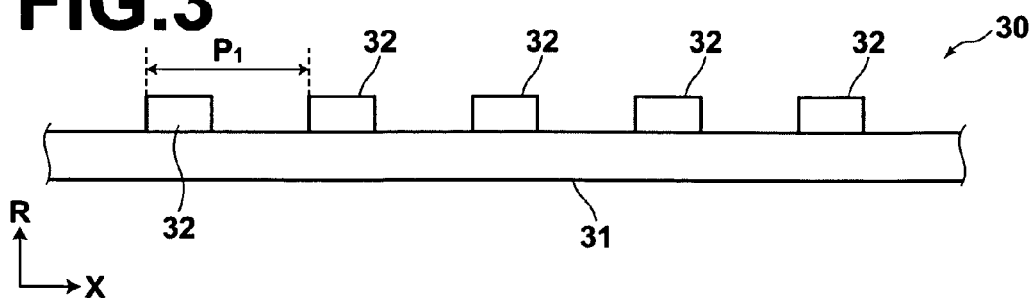
FIG. 3 is a schematic configuration diagram of a diffraction grating.

As shown in FIG. 3, diffraction grating 30 includes substrate 31 and a plurality of diffraction members 32 provided on substrate 31. Although, diffraction members 32 are formed on a planar surface in FIG. 3, they may be formed on a cylindrical surface concentric with periodic information imaging radiation image detector 40. In this case, the pitch of diffraction grating projected from radiation source 11 to the cylindrical surface needs to be uniform. Substrate 31 may be formed, for example, by glass or plastic and a material with a small thermal expansion coefficient is preferably used. Each of the plurality of diffraction members 32 is formed in a linear shape extending in one direction (thickness direction in FIG. 3). The arrangement pitch $P_1$ of the plurality of diffraction members 22 (period of the diffraction grating) is constant in the present embodiment. As for the material of member 22, for example, gold or silicon may be used. Preferably, member 22 forms a so-called phase modulation grating that gives a phase modulation of about 90° or about 180° to the emitted radiation. The thickness of gold required in the X-ray energy range of ordinary medical diagnosis is, for example, about one to several micrometers. An amplitude modulation grating may also be used. In this case, member 22 needs to have a thickness which is thick enough to sufficiently absorb radiation. For example, the thickness of gold required in the X-ray energy range of ordinary medical diagnosis, in this case, is about ten to several tens of micrometers.

If a radiation emission unit having a plurality of radiation focuses is used as radiation emission unit 10, it is preferable that the apparatus is configured such that an interval $P_0$ between focuses in X direction, a distance $L_1$ (FIG. 2) from the focus to diffraction grating 30, a distance $Z_1$ (FIG. 2) from diffraction grating 30 to periodic information imaging radiation image detector 40, and an interval $P_2$ (FIG. 10) between linear electrodes of periodic information imaging radiation image detector 40 satisfy Formula (1) below.

$$P_0 = P_2 \times \frac{L_1}{Z_1} \quad (1)$$

In order to make the structure of the radiation phase contrast imaging apparatus of the present embodiment function as a Talbot interferometer, several other conditions need to be substantially satisfied, which will be described hereinafter.

In order to make use of Talbot interference, the distance $Z_1$ from diffraction grating 30 to periodic information imaging radiation image detector 40 needs to substantially satisfy the following condition, if diffraction grating 30 is a phase modulation grating that gives a phase modulation of 90°.

$$Z_1 = \left(m + \frac{1}{2}\right)\frac{P_1^2}{\lambda} \quad (2)$$

where, $\lambda$ is the wavelength of radiation (normally, center wavelength), m is 0 or a positive integer, $P_1$ is the grating pitch of the diffraction members 32 described above.

Further, the distance $Z_1$ must substantially satisfy the condition below if diffraction grating 30 is a phase modulation grating that gives a phase modulation of 180° or an amplitude modulation grating.

$$Z_1 = (m+1)\frac{P_1^2}{\lambda} \quad (3)$$

Diffraction grating 30 of the present embodiment has a size corresponding to the emission range of a fan beam emitted from radiation emission unit 10 and transmitted through subject 20, and formed in a strip-like shape having a width in X direction larger than that in Y direction.

Figure 4:
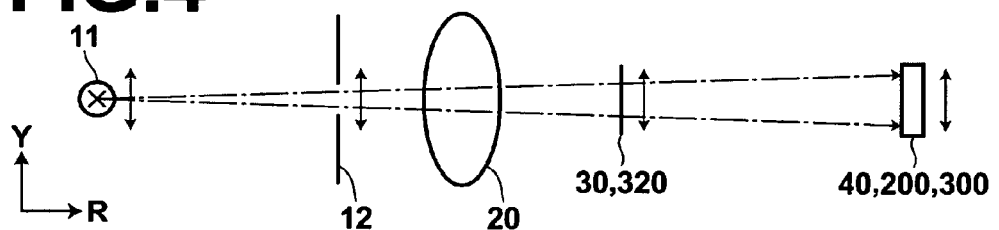
FIG. 4 illustrates an operation of a shifting mechanism.

As shown in FIG. 4, shifting mechanism 55 is a mechanism for integrally shifting radiation source 11, slit member 12, diffraction grating 30, and periodic information imaging radiation image detector 40 along Y direction. This shifting operation by shifting mechanism 55 causes subject 20 to be scanned with the fan beam outputted from radiation emission unit 10 in Y direction.

Figure 5:
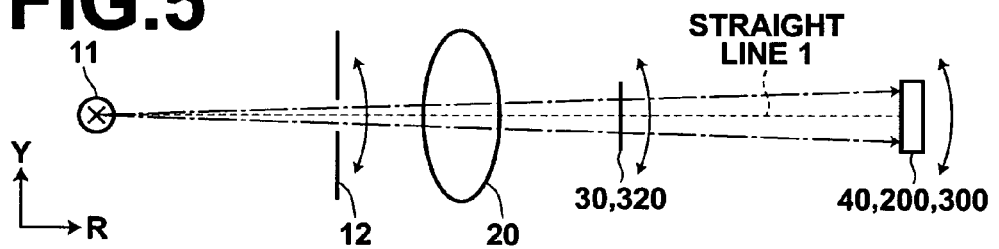
FIG. 5 illustrates an alternative operation of the shifting mechanism.

In the present embodiment, slit member 12, diffraction grating 30, and periodic information imaging radiation image detector 40 are shifted along Y direction as described above, but they may be integrally shifted along an arc with the radius centered on radiation source 11, the length of the line 1 connecting between radiation source 11 and periodic information imaging radiation image detector 40, as shown in FIG. 5.

The configuration of periodic information imaging radiation image detector 40 of the radiation phase contrast imaging apparatus of the present embodiment will now be described in detail.

Figure 6:
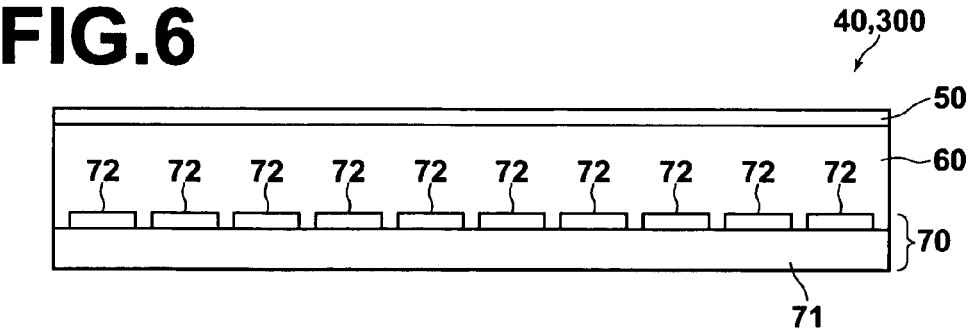
FIG. 6 is a cross-sectional view of a periodic information imaging radiation image detector of the radiation phase contrast imaging apparatus according to the first embodiment, illustrating a schematic configuration thereof.

FIG. 6 is a partial cross-sectional view of periodic information imaging radiation image detector 40.

As shown in FIG. 6, periodic information imaging radiation image detector 40 includes active matrix substrate 70, semiconductor layer 60 formed on substantially the entire surface of the active matrix substrate 70, and upper electrode 50.

Semiconductor layer 60 has electromagnetic wave conductivity and generates charges therein when exposed to radiation. As for semiconductor layer 60, for example, a selenium based amorphous Se film with a thickness of 10 to 1500 µm may be used. Alternatively, $PbI_2$, $HgI_2$, $Cd(Zn)Te$, $Bi_{12}TiO_{20}$, $Bi_{12}SiO_{20}$, or $Bi_{12}GeO_{20}$ may also be used.

Upper electrode 50 is formed of a conductive material having a low resistance, such as Au, Al, or the like, with a thickness capable of transmitting emitted radiation. Note that intermediate layers may be provided between upper electrode 50 and semiconductor layer 60. Such intermediate layers include a charge transport layer for preventing charge injection from upper electrode 50 and allowing charges of those generated in the semiconductor layer having opposite polarity to that of injected charges to reach upper electrode 50, a crystallization prevention layer for preventing crystallization of the amorphous Se, and the like.

As illustrated in FIG. 6, active matrix substrate 70 includes glass substrate 71 on which multiple unit elements 72, which include charge collection electrodes and switch elements corresponding to pixels forming radiation image of a subject, are disposed two-dimensionally. Active matrix substrate 70 is formed as a strip-like detector in which the number of unit elements in X direction is greater than the number of unit elements in Y direction.

Figure 7:
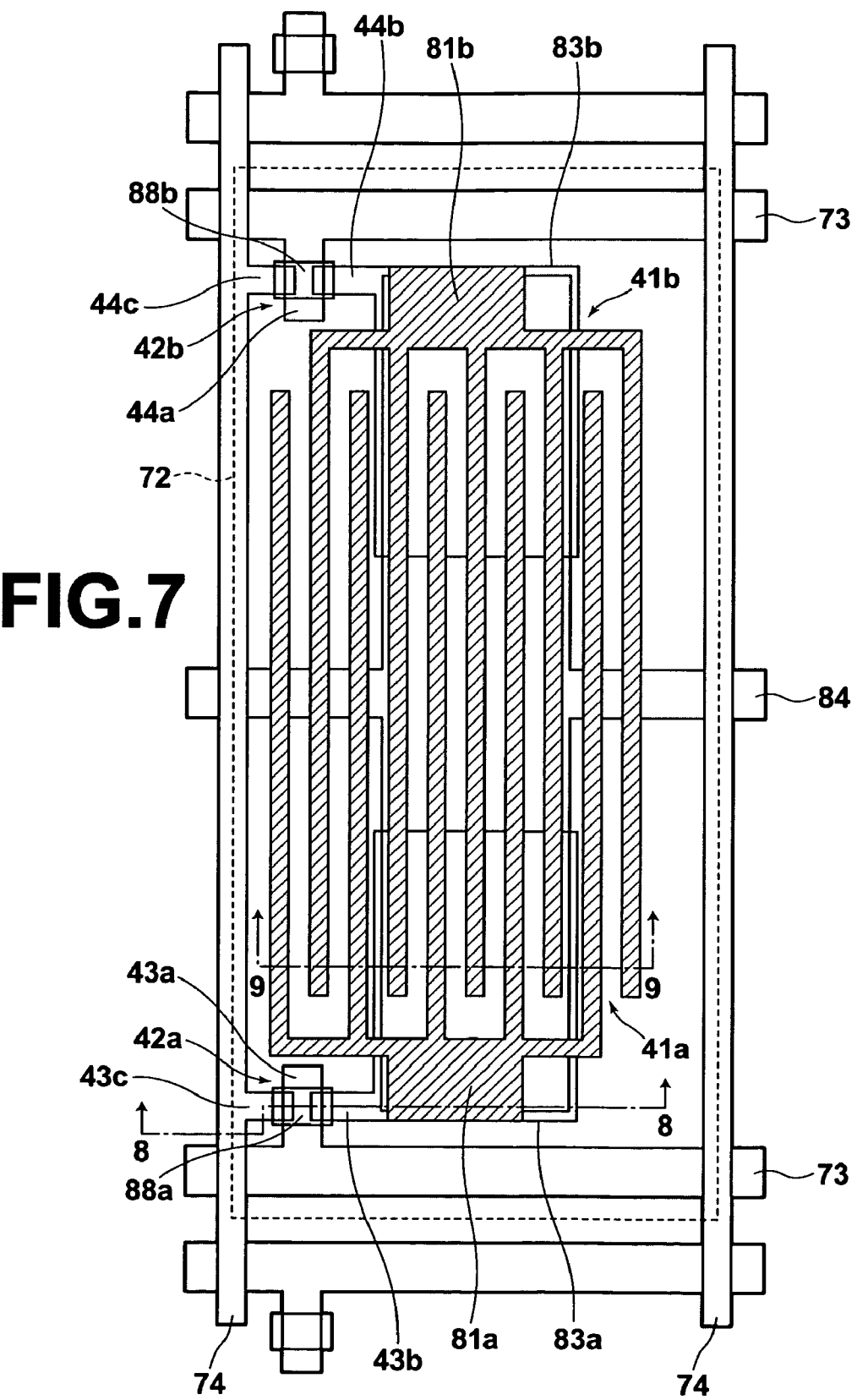
FIG. 7 is a partial plan view of the periodic information imaging radiation image detector of the radiation phase contrast imaging apparatus according to the first embodiment.
Figure 8:
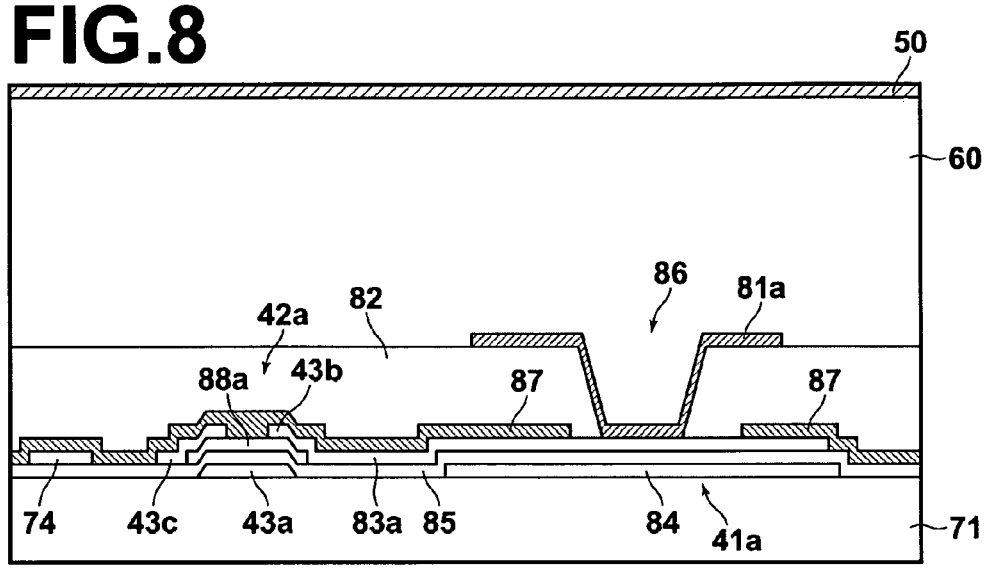
FIG. 8 is a partial cross-sectional view of the periodic information imaging radiation image detector taken along the line 8-8 in FIG. 7.
Figure 9:
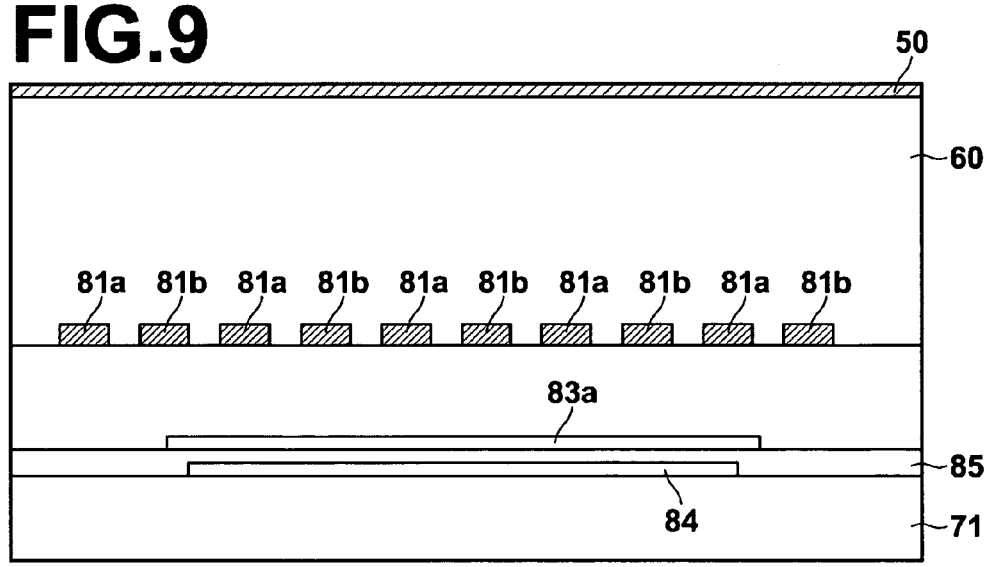
FIG. 9 is a partial cross-sectional view of the periodic information imaging radiation image detector taken along the line 9-9 in FIG. 7.

The structure of each pixel or sub-pixel of periodic information imaging radiation image detector 40 will now be described in detail. The term "sub-pixel" as used herein refers to a pair of two linear electrode groups alternately disposed such that the phase of the arrangement period become opposite to each other. FIG. 7 is a partial plan view of periodic information imaging radiation image detector 40, FIG. 8 is a cross-sectional view of periodic information imaging radiation image detector 40 taken along the line 8-8 in FIG. 7, and FIG. 9 is a cross-sectional view of periodic information imaging radiation image detector 40 taken along the line 9-9 in FIG. 7.

Periodic information imaging radiation image detector 40 includes a charge collection electrode, constituted by first linear electrode group 81a and second linear electrode group 81b, for collecting charges generated in semiconductor layer 60, first storage capacitor 41a for storing charges collected by first linear electrode group 81a, second storage capacitor 41b for storing charges collected by second linear electrode group 81b, a first TFT switch 42a for reading out the charges stored in first storage capacitor 41a, a second TFT switch 42b for reading out the charges stored in second storage capacitor 41b.

Figure 10:
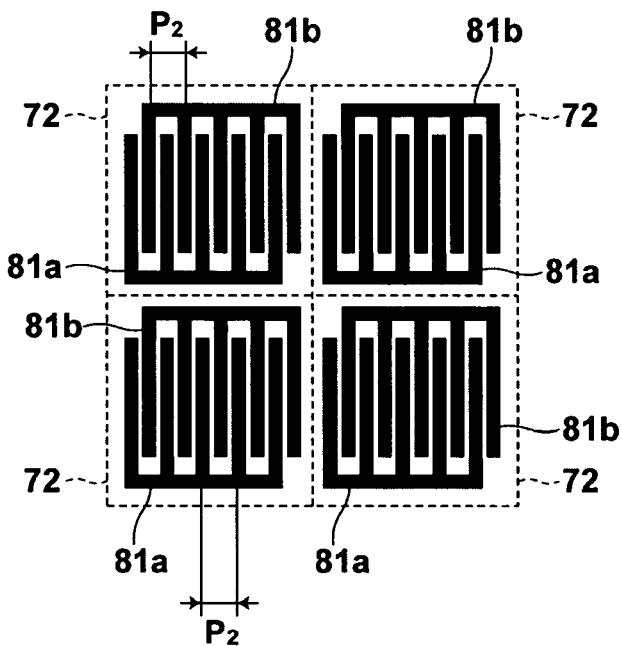
FIG. 10 is a schematic view of first linear electrode groups and second linear electrode groups of a unit element corresponding to four pixels.

FIG. 10 schematically illustrates first linear electrode groups 81a and second linear electrode groups 81b of unit element 72 corresponding to four pixels. Each of first linear electrode group 81a and second linear electrode group 81b includes multiple linear electrodes periodically disposed with a pitch of $P_2$. A linear electrode of second linear electrode group 81b is disposed between linear electrodes of first linear electrode group 81a such that the phase of the arrangement period of linear electrodes of first linear electrode groups 81a and the phase of the arrangement period of linear electrodes of second linear electrode group 81b are shifted by n (180°=a half of the pitch) from each other. As illustrated in FIG. 10, linear electrodes of first linear electrode group 81a are connected to each other, and linear electrodes of second linear electrode group 81b are connected to each other. Preferably, the connection wire connecting the linear electrodes is provided on a different plane from that of the linear electrodes so as not to function as an electrode, but the influence of the connection wire may be substantially reduced to a negligible level by reducing the width of the connection wire.

Arrangement pitch $P_2$ of linear electrodes of first linear electrode group 81a and arrangement pitch $P_2$ of linear electrodes of second linear electrode group 81b are set to a value in the range from 2 to 15 µm. The width of each linear electrode of first linear electrode group 81a and the width of each linear electrode of second linear electrode group 81b are in the range from 1 to 14 µm.

First linear electrode group 81a and second linear electrode group 81b may be formed, for example, of an amorphous transparent conductive oxide film.

Further, a charge transport layer for preventing charge injection from upper electrode 50 and allowing charges of those generated in semiconductor layer 60 to be collected by first linear electrode group 81a and second linear electrode group 81b and a crystallization prevention layer for preventing crystallization of the amorphous Se and the like may be provided between first and second linear electrode groups 81a, 81b and semiconductor layer 60.

First storage capacitor 41a is constituted by connection electrode 83a, gate insulation film 85, and charge storage capacitor electrode 84, in which gate insulation film 85 acts as a dielectric body and charges are stored between connection electrode 83a and charge storage capacitor electrode 84. Second storage capacitor 41b is constituted by connection electrode 83b, gate insulation film 85, and charge storage capacitor electrode 84, in which gate insulation film 85 acts as a dielectric body and charges are stored between connection electrode 83b and charge storage capacitor electrode 84.

First TFT switch 42a is constituted by gate electrode 43a formed by extending scanning wire 73, to be described later, drain electrode 43b formed by extending connection electrode 83a, source electrode 43c formed by extending data wire 74, to be described later, gate insulation film 85, semiconductor film 88a, and the like. Second TFT switch 42b is constituted by gate electrode 44a formed by extending scanning wire 73, drain electrode 44b formed by extending connection electrode 83b, source electrode 44c formed by extending data wire 74, gate insulation film 85, semiconductor film 88b, and the like. For example, gate insulation film 85 is formed of $SiN_x$, $SiO_x$, or the like. Semiconductor films 88a, 88b are channel sections of first and second TFT switches 42a, 42b, which are current paths connecting data wire 74 to connection electrodes 83a, 83b.

Insulation protection film 87 is formed so as to cover first storage capacitor 41a and second storage capacitor 41b, first TFT switch 42a and second TFT switch 42b, data wire 74, and the like. Contact holes 86 are formed in insulation protection film 87 at a connection section between first linear electrode group 81a and connection electrode 83a, and at a connection section between second linear electrode group 81b and connection electrode 83b.

Interlayer insulation film 82 is formed on insulation protection film 87 and contact holes 86 are formed through the interlayer insulation film 82, through which first linear electrode group 81a is connected to connection electrode 83a, and second linear electrode group 81b is connected to connection electrode 83b. Interlayer insulation film 82 is an organic insulation film to electrically insulate and isolate first TFT switch 42a from second TFT switch 42b. For example, an acrylic resin may be used as the material of the organic insulation film.

As illustrated in FIG. 7, scanning wires 73 and data wires 74 are electrode wires disposed in a grid pattern, and first TFT switch 42a or second TFT switch 42b is formed adjacent to each intersection point. Different scanning wires 73 are connected to first TFT switch 42a and second TFT switch 42b, and first TFT switch 42a and second TFT switch 42b are configured to be ON/OFF controlled independently.

A readout circuit (not shown) constituted by an amplifier for detecting a signal charge flowing out to data wire 74 is connected at the end of data wire 74. A gate driver (not shown) that outputs control signals for independently controlling first TFT switch 42a and second TFT switch 42b is connected to scanning wire 73.

Periodic information imaging radiation image detector 40 is disposed such that the extending direction of the linear electrodes thereof is perpendicular to the fan surface of the fan beam having a larger spread angle (fan surface extending along X-R surface in FIG. 1). That is, detector 40 is disposed such that the extending direction of the linear electrodes is parallel to Y direction in FIG. 1. Diffraction grating 30 is disposed such that the extending direction of diffraction members 32 is parallel to the extending direction of linear electrodes of periodic information imaging radiation image detector 40.

Periodic information imaging radiation image detector 40 of the present embodiment is formed along a cylindrical surface with a cylinder axis passing through radiation source 11 and parallel to linear electrodes of periodic information imaging radiation image detector 40.

Periodic information imaging radiation image detector 40 of the present embodiment may be specifically formed in the following manner. That is, providing a flexible substrate as substrate 71 of active matrix substrate 70, forming unit elements 72 on the flexible substrate, bonding the flexible substrate to a base material having the cylindrical surface, and forming semiconductor layer 60 and upper electrode 50 on active matrix substrate 71. It may be possible to bond the active matrix substrate 71 to a base material having the cylindrical surface after forming unit elements on the flexible substrate and forming semiconductor layer 60 and upper electrode 50 on active matrix substrate 71, but semiconductor layer 60 tends to be broken or detached if it is thick in that case. As substrate 71, a thin glass substrate reinforced with a plastic film may be used as substrate 71. Where light is emitted from the substrate side, it is preferable to use a transparent substrate and a transparent base material.

Shifting mechanism 55 is a mechanism for integrally shifting diffraction grating 30 and periodic information imaging radiation image detector 40 along Y direction as described above. It is also a mechanism for shifting, when diffraction grating 30 and periodic information imaging radiation image detector 40 are at a given position in Y direction, diffraction grating 30 or periodic information imaging radiation image detector 40 in a direction perpendicular to Y direction along the surface thereof from the position. For example, diffraction grating 30 or periodic information imaging radiation image detector 40 may be shifted by 1/n (n is an integer not less than two) of the arrangement pitch $P_1$ of the linear electrodes of periodic information imaging radiation image detector 40 and take a radiation image at each position, whereby image signals of n-types of phase components may be obtained. From the n types of image signals, the amount of differential phase shift with respect to each pixel, that is, an amount corresponding to a diffraction angle of radiation caused by subject 20 may be restored, which may be provided as a so-called phase contrast image through various types of image processing and representations. It is preferable, for example, to shift periodic information imaging radiation image detector 40 such that image signals corresponding to four or six types of phase components are obtained. When the charge collection electrode is formed of first linear electrode group 81a and second linear electrode group 81b, as in the present embodiment, four types of phase components may be obtained by shifting detector 40 by ½ of the arrangement pitch $P_2$ and six types of phase components may be obtained by shifting detector 40 by ⅓ of the arrangement pitch $P_2$. Next, an operation of the radiation phase contrast imaging apparatus according to the present embodiment for recording a radiation image and reading out from the periodic information imaging radiation image detector will be described.

First, subject 20 is placed between radiation emission unit 10 and diffraction grating 30 (FIG. 1). In the radiation phase contrast imaging apparatus according to the present embodiment, subject 20 is placed between radiation emission unit 10 and diffraction grating 30, but subject 20 may be placed between diffraction grating 30 and periodic information imaging radiation image detector 40. In this case, the distance from the subject to periodic information imaging radiation image detector 40 becomes shorter and the magnification ratio is reduced, which allows the apparatus to be easily installed in an existing radiography room. Further, it is particularly preferable, when an amplitude modulation grating is used as diffraction grating 30, to place subject 20 between diffraction grating 30 and periodic information imaging radiation image detector 40 from the viewpoint of decreasing radiation dose to subject 20.

Next, radiation is outputted from radiation source 11 of radiation emission unit 10 and emitted onto subject 20 after turning into a fan beam by passing through slit 12*a* of slit member 12. Radiation transmitted through subject 20 is emitted onto diffraction grating 30. The radiation emitted onto diffraction grating 30 is diffracted thereby and a self-image of diffraction grating 30 is formed at a predetermined distance from diffraction grating 30 in the optical axis direction of the radiation. For example, when diffraction grating 30 is a phase modulation grating that gives a phase modulation of 90°, a self-image of diffraction grating 30 is formed at a distance given by Formula (2) above (Formula (3) above, if diffraction grating 30 is a phase modulation grating that gives a phase modulation of 180° or an amplitude modulation grating). Here, the wavefront of radiation incident on diffraction grating 30 is distorted through the subject 20 so that the self-image of diffraction grating 30 is deformed accordingly.

Then, with a positive voltage being applied to upper electrode 50 of periodic information imaging radiation image detector 40 by a voltage source, the radiation representing a self-image formed by diffraction grating 30 in the manner as described above is emitted to periodic information imaging radiation image detector 40 from the side of upper electrode 50. In the radiation phase contrast imaging apparatus of the present embodiment, periodic information imaging radiation image detector 40 is disposed such that upper electrode 50 is oriented to the side of radiation emission unit 10.

The radiation emitted on periodic information imaging radiation image detector 40 transmits through upper electrode 50 and exposes semiconductor layer 60. Then, semiconductor layer 60 generates charge pairs by the exposure of the radiation, and negative charges of the charge pairs are combined with positive charges charged on upper electrode 50 and dissolved, while positive charges of the charge pairs are collected by first and second linear electrode groups 81*a*, 81*b* of each unit element 72, and stored in first and second storage capacitors 41*a*, 41*b*.

Figure 11:
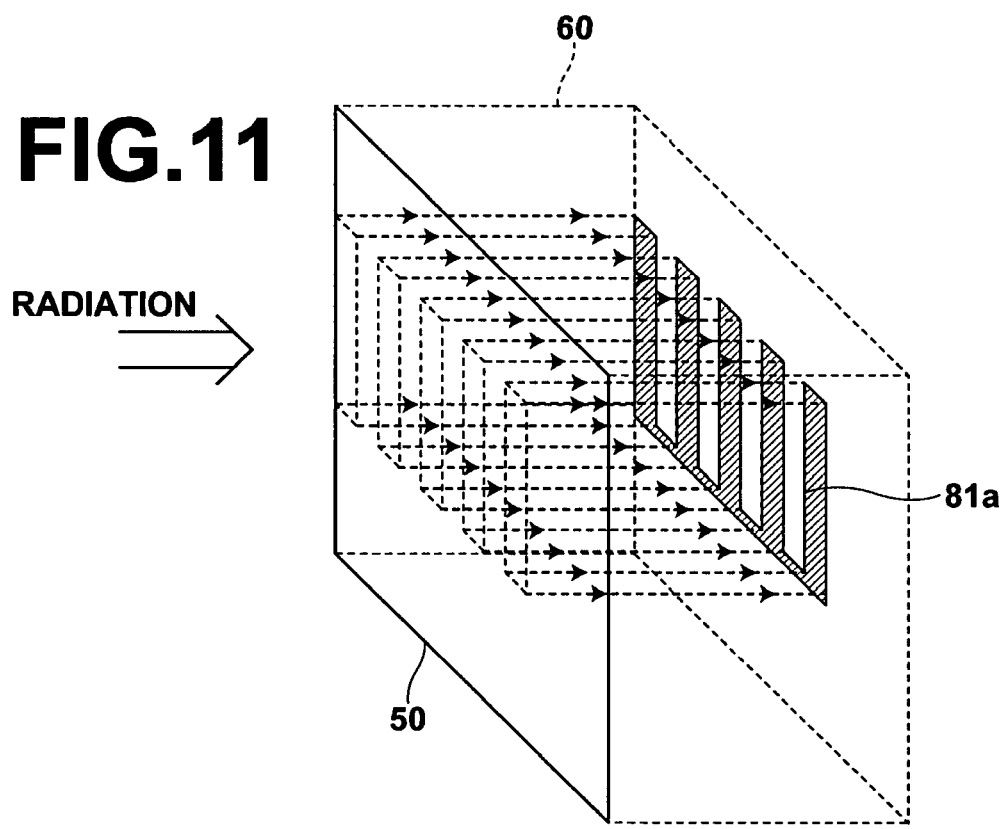
FIG. 11 illustrates an electric field formed in a semiconductor layer by the first linear electrode group.

Here, in periodic information imaging radiation image detector 40 of radiation phase contrast imaging apparatus of the present embodiment, the charge collection electrode for collecting charges generated in semiconductor layer 60 is constituted by first linear electrode group 81*a* and second linear electrode group 81*b*. Therefore, when a voltage is applied to upper electrode 50 in the manner as described above, electric fields are formed in semiconductor layer 60 toward first and second linear electrode groups substantially parallel to each other, i.e., substantially perpendicular to the surface of upper electrode 50, as illustrated by dotted arrows in FIG. 11. The charges generated in semiconductor layer 60 are collected by first and second linear electrode groups 81*a*, 81*b* along the electric fields, so that first and second linear electrode groups 81*a*, 81*b* perform a function equivalent to that of the combination of an amplitude diffraction grating and a detector provided in the later stage of the grating. Accordingly, charges representing image contrast generated by the superimposition of a self-image of the deformed diffraction grating 30 and a virtual diffraction grating formed by first linear electrode group 81*a* are stored in first charge capacitor 41*a*, and charges representing image contrast generated by the superimposition of a self-image of the deformed diffraction grating 30 and a virtual diffraction grating formed by second linear electrode group 81*b* are stored in second charge capacitor 41*b*. The image contrast described above generally takes the form of Moire fringes. As described above, first linear electrode group 81*a* and second linear electrode group 81*b* are phase shifted by $\pi$ from each other, thus signals corresponding to two types of phase components phase shifted from each other by $\pi$ are detected by periodic information imaging radiation image detector 40.

Then, control signals for turning ON first TFT switches 42*a* are sequentially outputted from the not shown gate driver to each scanning wire 73 connected to first TFT switches 42*a*. Then, first TFT switches 42*a* are turned ON according to the control signals outputted from the gate driver, and charges stored in first storage capacitor 41*a* of each unit element 72 are read out to data wire 74. The charge signal flowed out to data wire 74 is detected by the charge amplifier of a not shown readout circuit as an image signal corresponding to a first phase component.

Then, control signals for turning ON second TFT switches 42*b* are sequentially outputted from the not shown gate driver to each scanning wire 73 connected to second TFT switches 42*b*. Then, second TFT switches 42*b* are turned ON according to the control signals outputted from the gate driver, and charges stored in second storage capacitor 41*b* of each unit element 72 are read out to data wire 74. The charge signal flowed out to data wire 74 is detected by the charge amplifier of a not shown readout circuit as an image signal corresponding to a second phase component.

Thereafter, periodic information imaging radiation image detector 40 or diffraction grating 30 is shifted by shifting mechanism 55 in a direction perpendicular to Y direction, and the image recording in the detector and image signal reading from the detector are performed at each predetermined position, whereby image signals corresponding to the first and second phase components are detected at each predetermined position. Where the linear electrodes of periodic information imaging radiation image detector 40 or diffraction members of diffraction grating 30 are formed on a planar surface and disposed such that the extending direction thereof is parallel to Y direction in FIG. 1, the linear electrodes or diffraction members are projected from the radiation source onto cylindrical surface centered on an axis passing through the radiation source and is parallel to the extending direction at a uniform pitch. But, shifting a detector or a diffraction grating formed on a planar surface in a direction perpendicular to the extending direction with respect to the radiation source is undesirable because the pitch is varied. If such shifting is required, the detector or diffraction grating should be formed like a cylindrical surface.

Then, radiation source 11, slit member 12, diffraction grating 30, and periodic information imaging radiation image detector 40 are integrally shifted by a predetermined distance in Y direction by shifting mechanism 55 and the operation identical to that described above is repeated at the position.

Image signals detected in the manner as described above are inputted to phase image acquisition unit 6. Then, phase image acquisition unit 6 generates a phase image based on image signals of a plurality of phase components. More specifically, a partial phase image is generated based on image signals of a plurality of phase components obtained when slit member 12, diffraction grating 30, and periodic information imaging radiation image detector 40 are at a predetermined position in Y direction. Then, a complete phase image is generated by combining partial images obtained at respect positions in Y direction. Note that, as an alternative method, image signals for a complete phase image with respect to each phase component may be generated first and then an overall phase image may be generated based on the image signals with respect to each phase component. But the method in the present embodiment is preferable because the method is less influenced by the non-uniformity of the grating and detector.

Next, a modification of periodic information imaging radiation image detector 40 of radiation phase contrast imaging apparatus according to the first embodiment will be described.

Figure 12:
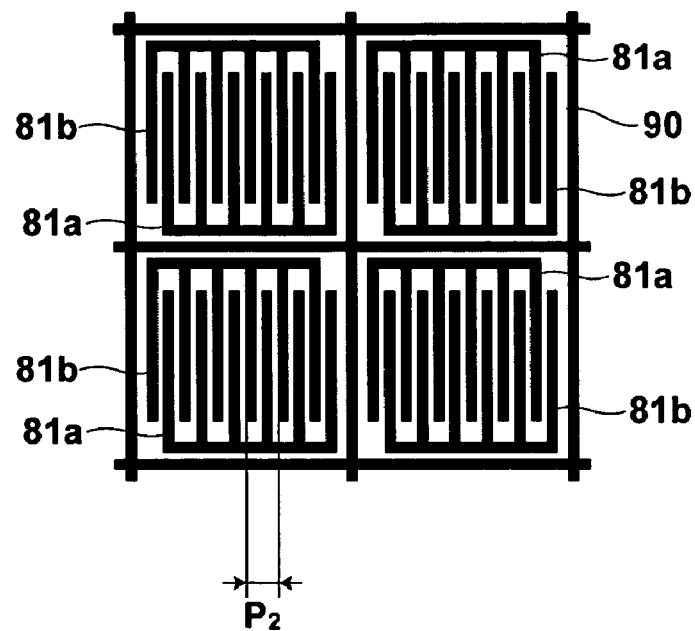
FIG. 12 illustrates a modification of the periodic information imaging radiation image detector of the radiation phase contrast imaging apparatus according to the first embodiment.

In addition to first linear electrode group 81a and second linear electrode group 81b of periodic information imaging radiation image detector 40 shown in FIG. 10, constant potential linear electrode 90 may be provided in a grid pattern enclosing the charge collection electrode, constituted by first and second linear electrode groups 81a, 81b, of each unit element 72, as illustrated in FIG. 12. A spatial gap between charge collection electrodes induces phase component contamination because charges from out of linear electrode are collected by electric fields distortion. Consequently, the provision of constant potential linear electrode 90 to which a constant potential is applied allows stabilization of the electric fields and prevention of the contamination described above. A potential that does not cause a large potential difference with an adjacent charge collection electrode is applied to constant potential linear electrode 90. That is, substantially the same potential as that of the charge collection electrode is applied. More specifically, constant potential linear electrode 90 is set to a ground potential or a value close to the ground potential. Where constant potential linear electrode 90 is provided, it is preferable to arrange and dispose first linear electrode group 81a and second linear electrode group 81b in the manner shown in FIG. 12.

In periodic information imaging radiation image detector 40 of the present embodiment, first linear electrode group 81a and second linear electrode group 81b, phase shifted by $\pi$ from each other, are provided in each unit element 72 as the charge collection electrode. The shape of the charge collection electrode is not limited to this.

Figure 13:
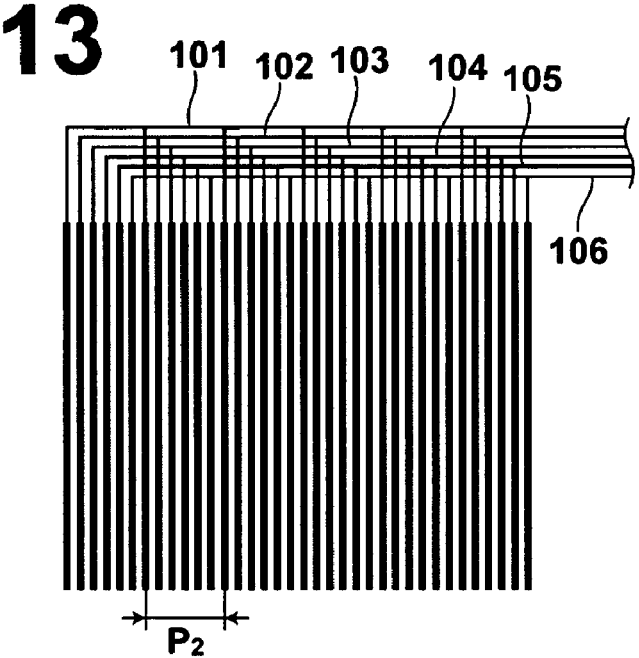
FIG. 13 illustrates a modification of the periodic information imaging radiation image detector.

For example, first to sixth linear electrode groups 101 to 106, each having multiple linear electrodes arranged with pitch $P_2$, may be disposed such that the phase of the arrangement period of linear electrodes of each linear electrode group is shifted by $\pi/3$ from each other, as illustrated in FIG. 13. More specifically, first to sixth linear electrode groups 101 to 106 may be disposed such that, when the phase of first linear electrode group 101 is 0, the phase of second linear electrode group 102 is $\pi/3$, the phase of third linear electrode group 103 is $2\pi/3$, the phase of fourth linear electrode group 104 is $\pi$, the phase of fifth linear electrode group 105 is $4\pi/3$, and the phase of sixth linear electrode group 106 is $5\pi/3$.

Formation of the charge collection electrode in the manner illustrated in FIG. 13 to read out charges collected by first to sixth linear electrode groups 101 to 106 with respect to each linear electrode group allows acquisition of image signals corresponding to six types of phase components having different phases by one image acquiring operation.

Figure 14:
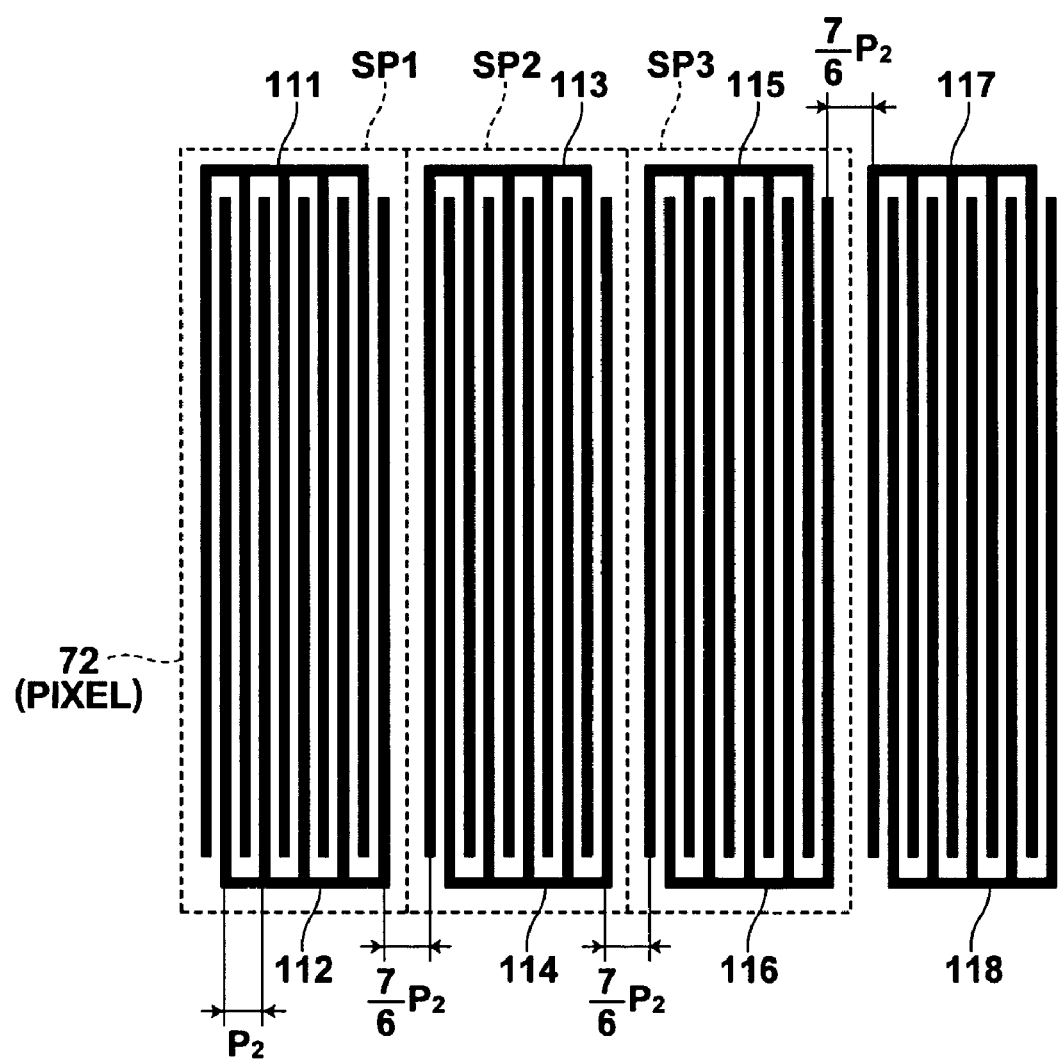
FIG. 14 illustrates a modification of the periodic information imaging radiation image detector of the radiation phase contrast imaging apparatus according to the first embodiment.

Further, as illustrated in FIG. 14, a pixel corresponding to one unit element 72 may be divided into a plurality of sub-pixels (here, three sub-pixels) and linear electrode groups having different phases may be disposed in each sub-pixel. In the present embodiment, the sub-pixel refers to a pair of two linear electrode groups alternately disposed such that the phase of the arrangement period is opposite to each other. More specifically, in the modification shown in FIG. 14, first linear electrode group 111 in which linear electrodes are arranged with pitch $P_2$ and second linear electrode group 112 in which linear electrodes are arranged with pitch $P_2$ are disposed in sub-pixel SP1 so as to have a phase difference of $\pi$ from each other, third linear electrode group 113 in which linear electrodes are arranged with pitch $P_2$ and fourth linear electrode group 114 in which linear electrodes are arranged with pitch $P_2$ are disposed in sub-pixel SP2 so as to have a phase difference of $\pi$ from each other, and fifth linear electrode group 115 in which linear electrodes are arranged with pitch $P_2$ and sixth linear electrode group 116 in which linear electrodes are arranged with pitch $P_2$ are disposed in sub-pixel SP3 so as to have a phase difference of $\pi$ from each other. Then, adjacent linear electrode groups of sub-pixel SP1 and sub-pixel SP2 are disposed at a distance of $(7/6) \times$ pitch $P_2$, and adjacent linear electrode groups of sub-pixel SP2 and sub-pixel SP3 are disposed at a distance of $(7/6) \times$ pitch $P_2$, whereby the phase is shifted by $4\pi/3$ between sub-pixels. Arrangement of the linear electrode groups in one pixel in the manner shown in FIG. 23 results in that, when the phase of first linear electrode group 111 is 0, the phase of second linear electrode group 112 is $\pi$, the phase of third linear electrode group 113 is $4\pi/3$, the phase of fourth linear electrode group 114 is $\pi/3$, the phase of fifth linear electrode group 115 is $2\pi/3$, and the phase of sixth linear electrode group 116 is $5\pi/3$. Note that linear electrode group 117 and linear electrode group 118 are the linear electrode groups of adjacent pixel.

Formation of the charge collection electrode in the manner illustrated in FIG. 14 to read out charges collected by first to sixth linear electrode groups 111 to 116 with respect to each linear electrode group allows acquisition of image signals corresponding to six types of phase components by one image acquiring operation. The structure of charge collection electrode shown in FIG. 13 also allows acquisition of image signals corresponding to six types of phase components by one image acquiring operation, but the structure of charge collection electrode shown in FIG. 14 allows the use of wider linear electrodes in comparison with the structure of FIG. 13. The spatial resolution is somewhat degraded in the structure shown in FIG. 14, but the structure allows easy connection of linear electrodes.

Figure 15:
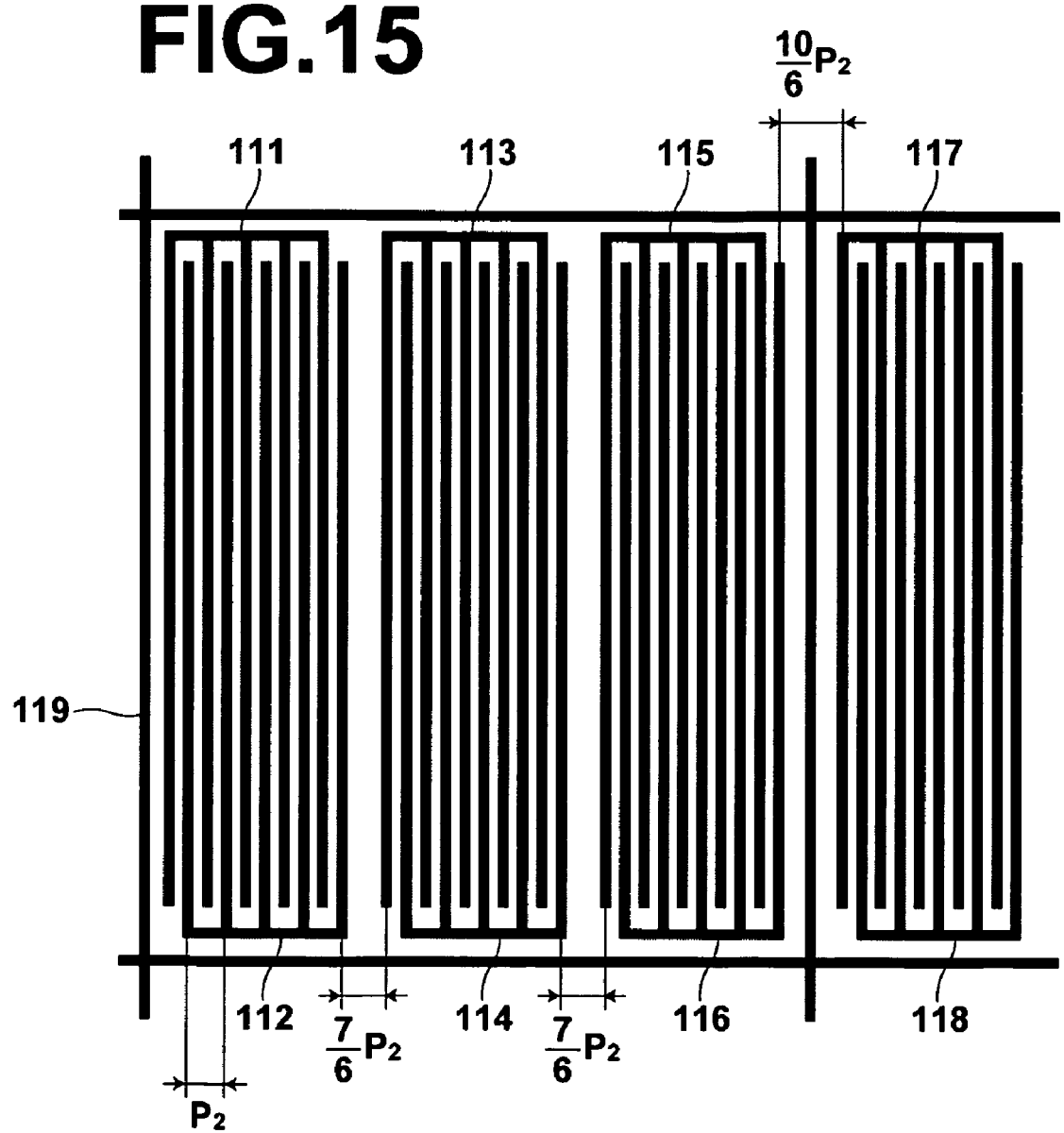
FIG. 15 illustrates a modification of the periodic information imaging radiation image detector of the radiation phase contrast imaging apparatus according to the first embodiment.

In addition to first to sixth linear electrode groups 111 to 116 shown in FIG. 14, constant potential electrode 119 may be provided in a grid pattern enclosing the charge collection electrode, constituted by first to sixth linear electrodes 111 to 116, of each unit element 72, as illustrated in FIG. 15. The effect of the constant potential electrode 119 is identical to that described in relation to FIG. 12. A potential that does not cause a large potential difference with an adjacent charge collection electrode is applied to constant potential electrode 119. That is, substantially the same potential as that of the charge collection electrode is applied. More specifically, constant potential electrode 119 is set to a ground potential or a value close to the ground potential. Where constant potential electrode 119 is provided, the pitch between linear electrode groups of adjacent pixels in a direction perpendicular to the linear electrodes, i.e., between linear electrode group 116 and linear electrode group 117, is set to $(10/6) \times P_2$, as shown in FIG. 15.

Figure 16:
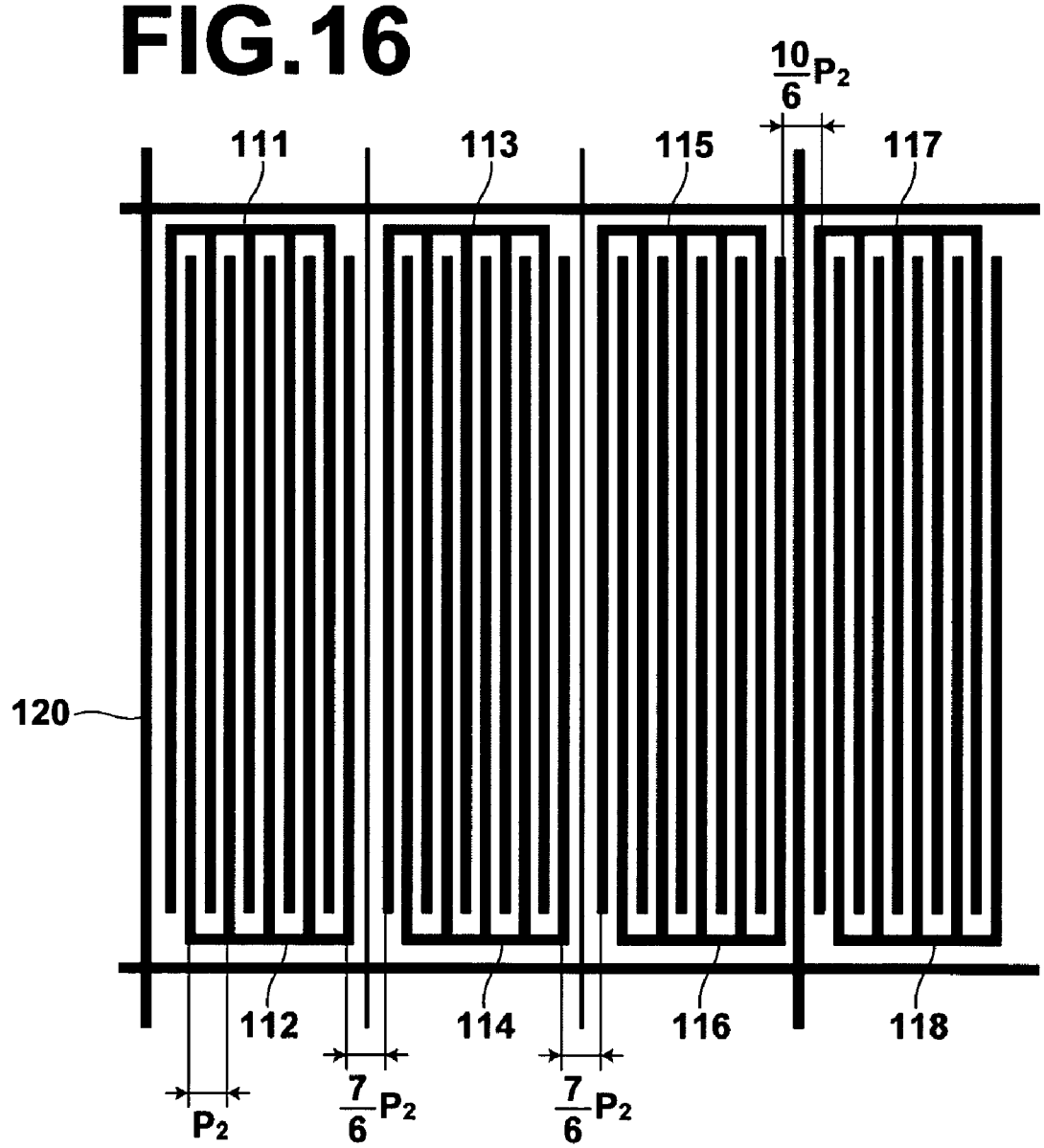
FIG. 16 illustrates a modification of the periodic information imaging radiation image detector of the radiation phase contrast imaging apparatus according to the first embodiment.

Instead of providing constant potential electrode 119 to enclose each pixel, as shown in FIG. 15, constant potential electrode 120 may be provided to enclose each sub-pixel, as shown in FIG. 16.

Figure 17:
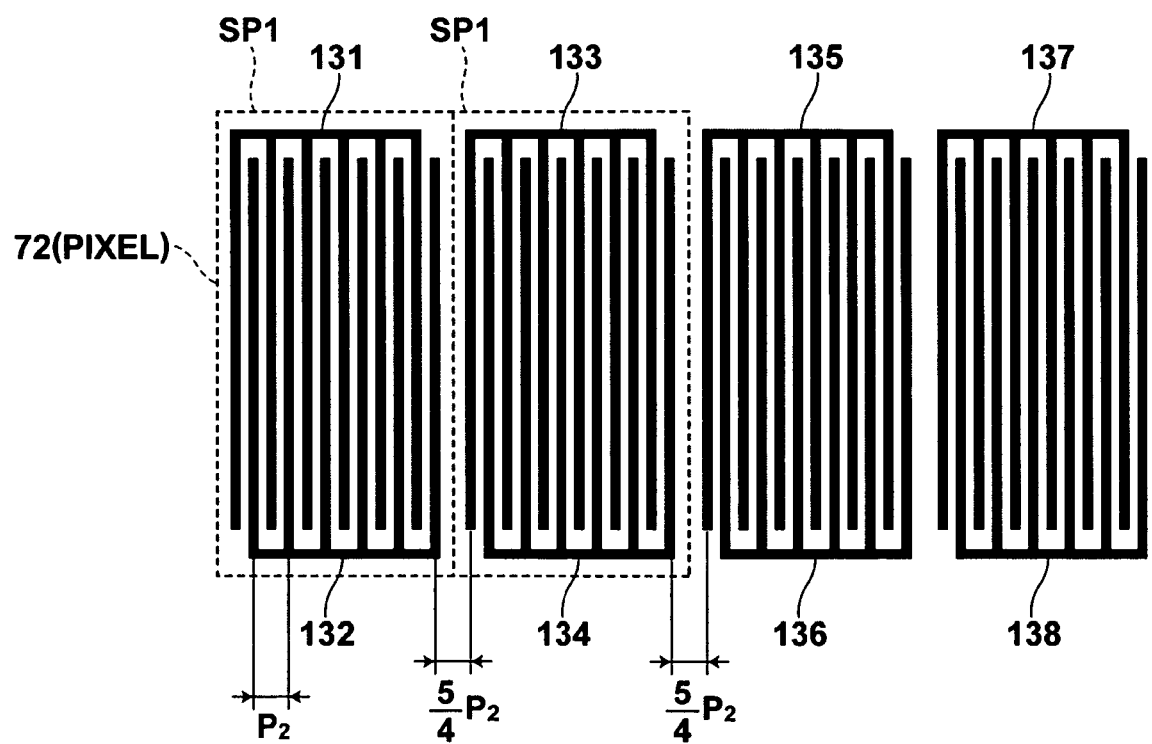
FIG. 17 illustrates a modification of the periodic information imaging radiation image detector of the radiation phase contrast imaging apparatus according to the first embodiment.

Further, as illustrated in FIG. 17, a pixel corresponding to one unit element 72 may be divided into two sub-pixels, and linear electrode groups having different phases may be disposed in each sub-pixel. More specifically, in the modification shown in FIG. 17, first linear electrode group 131 in which linear electrodes are arranged with pitch $P_2$ and second linear electrode group 132 in which linear electrodes are arranged with pitch $P_2$ are disposed in sub-pixel SP1 so as to have a phase difference of $\pi$ from each other, third linear electrode group 133 in which linear electrodes are arranged with pitch $P_2$ and fourth linear electrode group 134 in which linear electrodes are arranged with pitch $P_2$ are disposed in sub-pixel SP2 so as to have a phase difference of $\pi$ from each other. Then, adjacent linear electrode groups of sub-pixel SP1 and sub-pixel SP2 are disposed at a distance of $(5/4) \times P_2$. This arrangement results in that, when the phase of first linear electrode group 131 is assumed to be 0, the phase of second linear electrode group 132 is $\pi$, the phase of third linear electrode group 133 is $3\pi/2$, the phase of fourth linear electrode group 134 is $\pi/2$, that is, first to fourth linear electrode groups correspond to the phases shifted by $\pi/2$ from each other. Linear electrode groups 135 to 138 are linear electrode groups of adjacent pixel. Linear electrode group 135 detects a signal having the same phase as that of first linear electrode group 131, linear electrode group 136 detects a signal having the same phase as that of second linear electrode group 132, linear electrode group 137 detects a signal having the same phase as that of third linear electrode group 133, and linear electrode group 138 detects a signal having the same phase as that of fourth linear electrode group 134.

Formation of the charge collection electrode in the manner illustrated in FIG. 17 to read out charges collected by first to fourth linear electrode groups 131 to 134 with respect to each linear electrode group allows acquisition of image signals corresponding to four types of phase components by one image acquiring operation.

FIG. 14 or 17 illustrates a case where a pixel corresponding to one unit element 72 is divided into three or two sub-pixels, but the pixel may be divided into n ($n \geq 4$) sub-pixels. In this case, if the pitch between adjacent linear electrode groups of adjacent sub-pixels is set to $(2n+1)P_2/2n$, linear electrode groups corresponding to phases shifted by $\pi/n$ from each other may be provided.

When a pixel is divided into two to three sub-pixels, data of four to six phase components may be obtained by one image acquiring operation, and a preferable phase image may be obtained without shifting periodic information imaging radiation image detector 40 by 1/n of the pitch of the linear electrodes. When obtaining data of four to six phase components without dividing a pixel into sub-pixels, the structure shown in FIG. 13 may be used, but each linear electrode has a narrow width, which may cause a manufacturing problem. On the other hand, $n \geq 4$ while maintaining the pixel size causes each linear electrode group to have a less number of linear electrodes, whereby the accuracy as the data of phase components is degraded.

When diving a pixel into a plurality of sub-pixels in the manner as described above, it is preferable to set the width of the pair of linear electrode groups in the length direction of the linear electrodes in each sub-pixel greater than the width of the pair of linear electrode groups in a direction perpendicular to the length direction of the linear electrodes, as illustrated in FIGS. 14 to 17.

Figure 18:
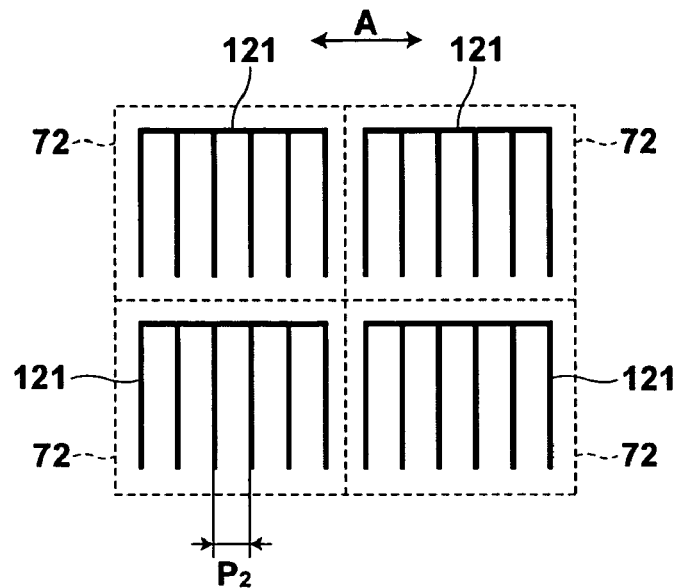
FIG. 18 illustrates a modification of the periodic information imaging radiation image detector of the radiation phase contrast imaging apparatus according to the first embodiment.

The modifications described above are examples in which a plurality of linear electrode groups is provided in each unit element 72. But, for example, only one linear electrode group 121, in which linear electrodes are arranged with pitch $P_2$, may be provided in each unit element 72, as illustrated in FIG. 18. FIG. 18 illustrates linear electrode groups 121 of four adjacent unit elements 72. As illustrated in FIG. 18, where the charge collection electrode of unit element 72 is formed of one linear electrode group and image signals corresponding to a plurality of types of phase components having different phases are obtained, periodic information imaging radiation image detector 40 or diffraction grating 30 may be shifted relative to each other by shifting mechanism 55 in a direction perpendicular to linear electrodes (arrow A direction in FIG. 18) along the plane thereof and radiation image taking may be performed a plurality of times according to the shifting. For example, image signals corresponding to three types of phase components may be obtained by performing the shifting by 1/3 of pitch $P_2$ and taking a radiation image at each position. Otherwise, image signals corresponding to six types of phase components may be obtained by performing the shifting by 1/6 of pitch $P_2$ and taking a radiation image at each position.

Figure 19:
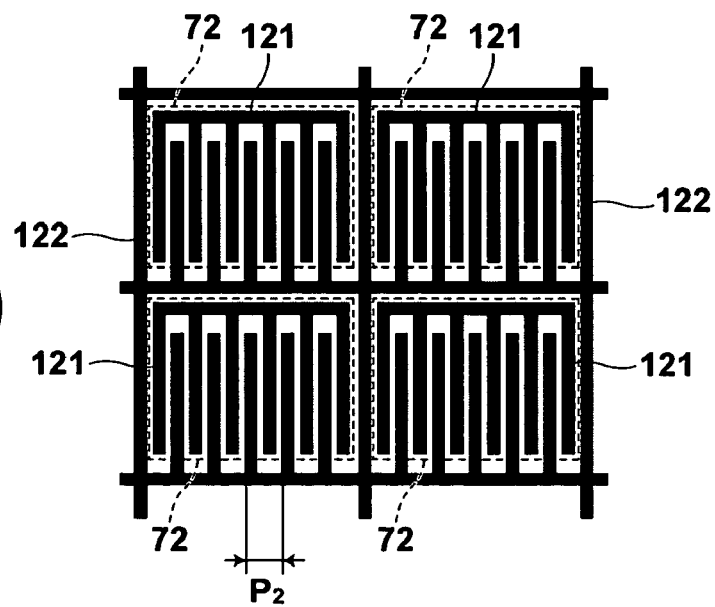
FIG. 19 illustrates a modification of the periodic information imaging radiation image detector of the radiation phase contrast imaging apparatus according to the first embodiment.

In addition to the charge collection electrodes of linear electrode groups 121 shown in FIG. 18, constant potential electrode 122 may be provided as illustrated in FIG. 19. Constant potential electrode 122 is arranged so as to be disposed between each linear electrode of each linear electrode group 121 and in a grid pattern to enclose each unit element 72. The effect of the constant potential electrode 122 is identical to that described in relation to FIG. 12. A potential that does not cause a large potential difference with an adjacent charge collection electrode is applied to constant potential electrode 122. That is, substantially the same potential as that of the charge collection electrode is applied. More specifically, constant potential electrode 122 is set to a ground potential or a value close to the ground potential.

In FIG. 10, the description has been made of a case in which first linear electrode group 81a and second linear electrode group 81b are phase shifted by $\pi$ from each other, but instead, three linear electrode groups phase shifted by $2\pi/3$ from each other may be provided in each unit element 72. Formation of the charge collection electrode in the manner described above allows the acquisition of image signals corresponding to three types of phase components by one image acquiring operation. That is, the number of image acquiring operations may be reduced 1/3 in comparison with a radiation image detector with one linear electrode group for each unit element 72. Further, if the charge collection electrode of each unit element 72 is formed of three linear electrode groups in the manner as described above and a shifting mechanism for relatively shifting periodic information imaging radiation image detector 40 and diffraction grating 30 is provided, and if shifting is performed, for example, by 1/2 of pitch $P_2$ to take a radiation image at each position, image signals corresponding to six types of phase components may be obtained.

The radiation phase contrast imaging apparatus according to the first embodiment uses a radiation image detector having TFT switches, but a CMOS or a CCD may also be used as the switch element.

Further, in the radiation phase contrast imaging apparatus according to the first embodiment, as periodic information imaging radiation image detector 40, a detector to which a positive voltage is applied when recording a radiation image is used. Alternatively, a TFT readout type radiation image detector to which a negative voltage is applied when recording a radiation image may be used.

Still further, in the radiation phase contrast imaging apparatus according to the first embodiment, periodic information imaging radiation detector 40 is disposed along a cylindrical surface. Diffraction grating 30 may also be disposed along a cylindrical surface as in periodic information imaging radiation detector 40.

Next, a second embodiment of the radiation phase contrast imaging apparatus of the present invention will be described. The radiation phase contrast imaging apparatus according to the second embodiment uses an optical readout type periodic information imaging radiation image detector, instead of the TFT readout type periodic information imaging radiation image detector of the radiation phase contrast imaging apparatus according to the first embodiment. The radiation phase contrast imaging apparatus according to the second embodiment differs from the radiation phase contrast imaging apparatus according to the first embodiment only in the structure of the periodic information imaging radiation image detector. Accordingly, only the structure of the periodic information imaging radiation image detector will be described. FIG. 20A is a perspective view of the periodic information imaging radiation image detector, FIG. 20B is an XZ cross-sectional view of the periodic information imaging radiation image detector shown in FIG. 20A, and FIG. 20C is an XY cross-sectional view of the periodic information imaging radiation image detector shown in FIG. 20A.

As illustrated in FIGS. 20A to 20C, periodic information imaging radiation image detector 200 of the radiation phase contrast imaging apparatus according to the second embodiment includes the following stacked in the order listed below: first electrode layer 201 that transmits radiation; recording photoconductive layer 202 that generates charges by receiving radiation transmitted through first electrode layer 201; charge transport layer 204 that acts as an insulator against charges of one polarity of those generated in recording photoconductive layer 202 and as a conductor for charges of the other polarity; readout photoconductive layer 205 that generates charges by receiving readout light; and second electrode layer 206. Storage section 203 for storing charges generated in recording photoconductive layer 202 is formed adjacent to the interface between recording photoconductive layer 202 and charge transport layer 204. Each of the layers described above is stacked on glass substrate 207 one after another from second electrode layer 206.

As for first electrode layer 201, any material may be used as long as it transmits radiation. For example, a NESA film ($SnO_2$), ITO (Indium Tin Oxide), IZO (Indium Zinc Oxide), IDIXO (Idemitsu Indium X-metal Oxide: Idemitsu Kosan Co., Ltd) which is an amorphous light transmissive oxide film, or the like with a thickness of 50 to 200 nm may be used. Alternatively, Al or Au with a thickness of 100 nm may be used.

Second electrode layer 206 includes a plurality of transparent linear electrodes 206a that transmits readout light and a plurality of opaque linear electrodes 206b that blocks the readout light. Transparent linear electrodes 206a and opaque linear electrodes 206b extend from one end of an image forming area of periodic information imaging radiation image detector 200 to the other end continuously and straightly. As illustrated in FIGS. 20A and 20B, transparent linear electrodes 206a and opaque linear electrodes 206b are disposed alternately in parallel at a predetermined distance.

Transparent linear electrodes 206a are formed of a material that transmits readout light and has conductivity. For example, ITO, IZO, or IDIXO may be used as in first electrode layer 201. The thickness of each electrode 206a is about 100 to 200 nm.

Opaque linear electrodes 206b are formed of a material that blocks the readout light and has conductivity. It is preferable that opaque linear electrodes 206b transmit erasure light, and a combination of one of the transparent conductive materials described above with a color filter is used as the opaque linear electrode 206b. The thickness of the transparent conductive material is about 100 to 200 nm.

As will be described later, an image signal is read out by adjacent transparent linear electrode 206a and opaque linear electrode 206b as a pair. In periodic information imaging radiation image detector 200 of the present embodiment, 20 pairs of transparent linear electrode 206a and opaque linear electrode 206b are disposed in the width of one pixel constituting a radiation image, as illustrated in FIG. 21. That is, 20 linear electrode pairs from first linear electrode pair 211, second linear electrode pair 212, third linear electrode pair 213, and so forth are disposed within the width of one pixel. Here, in the present invention, the "pixel unit" of second embodiment refers only to the division in a direction perpendicular to the linear electrodes. As illustrated in FIG. 20, the linear electrode pairs are disposed such that the distance between every other pairs, e.g., the distance between first linear electrode pair 211 and third linear electrode pair 213, or the distance between second linear electrode pair 212 and fourth linear electrode pair 214, corresponds to pitch $P_2$. Pitch $P_2$ is set to a value in the range from 2 to 15 μm. A first linear electrode group is formed of $(2n-1)^{th}$ (n is an integer not smaller than 1 and not greater than 10) linear electrode pairs and a second linear electrode group is formed of $(2n)^{th}$ (n is an integer not smaller than 1 and not greater than 10) linear electrode pairs. Then, the first and second linear electrode groups within the width of one pixel described above are alternately disposed repeatedly in the direction perpendicular to the length direction of the linear electrodes. In this case, first linear electrode groups and second linear electrode groups are disposed such that the phase of arrangement period of each linear electrode pair is shifted by π from each other. Although not shown, transparent linear electrodes 206a of the first linear electrode groups are physically connected to each other with a connection wire, such as a lead wire. Also, transparent linear electrodes 206a of the second linear electrode groups are physically connected to each other with a connection wire, such as a lead wire.

Recording photoconductive layer 202 may be formed of any material as long as it generates charges when exposed to radiation. Here, a-Se based material having excellent properties, such as relatively high quantum efficiency to radiation and high dark resistance, is used. An appropriate layer thickness is in the range from 10 to 1500 μm. For a mammography application, in particular, a preferable layer thickness is in the range from 150 to 250 μm, and for a general radiography application, a preferable layer thickness is in the range from 500 to 1200 μm.

As for the material of charge transport layer 204, for example, a material having a greater difference in charge mobility between charges charged on first electrode layer 201 when a radiation image is recorded and the charges having opposite polarity (for example, not less than $10^2$, more preferably, not less than $10^3$), is preferably used. In this respect, organic compounds such as poly N-vinylcarbazole (PVK), N,N'-diphenyl-N,N'-bis(3-methylphenyl)-[1,1'-biphenyl]-4,4'-diamine (TPD), discotic liquid crystal, and the like, or semiconductor materials such as TPD-dispersed polymers (polycarbonate, polystyrene, PVK), a-Se doped with 10 to 200 ppm of Cl, $As_2Se_3$, and the like are preferably used. An appropriate thickness of charge transport layer is in the range from 0.2 to 2 μm.

Readout photoconductive layer 205 may be formed of any material as long as it shows conductivity when exposed to readout light. For example, a photoconductive material consisting primarily of at least one of a-Se, Se—Te, Se—As—Te, non-metal phthalocyanine, metal phthalocyanine, MgPc (magnesium phthalocyanine) VoPc (phase II of Vanadyl phthalocyanine, CuPc (cupper phthalocyanine), and the like is preferably used. An appropriate thickness of photoconductive layer 205 is in the range from 5 to 20 µm.

Periodic information imaging radiation image detector 200 is disposed such that the extending direction of the linear electrodes thereof is perpendicular to the fan surface of the fan beam having a larger spread angle (fan surface extending along X-R surface in FIG. 1). That is, detector 200 is disposed such that the extending direction of the linear electrodes is parallel to Y direction in FIG. 1. Diffraction grating 30 is disposed such that the extending direction of diffraction members 32 is parallel to the extending direction of linear electrodes of periodic information imaging radiation image detector 200.

Periodic information imaging radiation image detector 200 of the present embodiment is formed along a cylindrical surface with an axis passing through radiation source 11 and parallel to linear electrodes of periodic information imaging radiation image detector 200 as the central axis.

Next, an operation of the radiation phase contrast imaging apparatus according to the second embodiment for recording a radiation image to and reading out from the periodic information imaging radiation image detector will be described.

The operation steps from the emission of radiation from radiation emission unit 10 to the formation of a self-image by diffraction grating 30 are identical to those of the radiation phase contrast imaging apparatus according to the first embodiment, and therefore will not be elaborated upon further here.

Thereafter, as illustrated in FIG. 22A, with a negative voltage being applied to first electrode layer 201 of periodic information imaging radiation image detector 200 by high voltage source 300, radiation representing a self-image of diffraction grating 30 formed by grating 30 is emitted to periodic information imaging radiation image detector 200 from the side of first electrode layer 201.

The radiation emitted onto periodic information imaging radiation image detector 200 transmits through first electrode layer 201 and reaches recording photoconductive layer 202. Then, recording photoconductive layer 202 generates charge pairs by the exposure of the radiation, and positive charges of the charge pairs are combined with negative charges charged on the first electrode layer 201 and dissolved, while negative charges of the charge pairs are stored, as latent image charges, in storage section 203 formed at the interface between recording photoconductive layer 202 and charge transport layer 204 (FIG. 22B).

Here, in periodic information imaging radiation image detector 200 of radiation phase contrast imaging apparatus of the present embodiment, second electrode layer 206 for collecting charges generated in recording photoconductive layer 202 to storage section 203 is constituted by transparent linear electrode 206a and opaque linear electrode 206b. Therefore, when a voltage is applied to first electrode layer 201 in the manner as described above, electric fields are formed in recording photoconductive layer 202 from transparent linear electrode 206a and opaque linear electrode 206b toward first electrode layer 201 substantially parallel to each other, i.e., substantially perpendicular to the surface of first electrode layer 201. Negative charges generated in recording photoconductive layer 202 are moved toward each linear electrode along the electric field without spreading and collected in storage section 203, so that transparent linear electrode 206a and opaque linear electrode 206b perform a function equivalent to that of the combination of an amplitude diffraction grating and a detector provided in the later stage of the grating. Accordingly, charges representing an intensity modified signal through superimposition of the deformed self-image of diffraction grating 30 with a virtual grating formed by the first linear electrode group constituted by $(2n-1)^{th}$ (n is an integer not smaller than 1 and not greater than 10) linear electrode pairs shown in FIG. 21 are stored in a portion of storage section 203 above the first linear electrode group, and charges representing an intensity modified signal through superimposition of the deformed self-image of diffraction grating 30 with a virtual grating formed by the second linear electrode group constituted by $(2n)^{th}$ (n is an integer not smaller than 1 and not greater than 10) linear electrode pairs shown in FIG. 21 are stored in a portion of storage section 203 above the second linear electrode group. As described above, the first linear electrode group and second linear electrode group are phase shifted by $\pi$ from each other, so that signals corresponding to two types of phase components phase shifted from each other by $\pi$ are detected by periodic information imaging radiation image detector 200.

Figure 23:
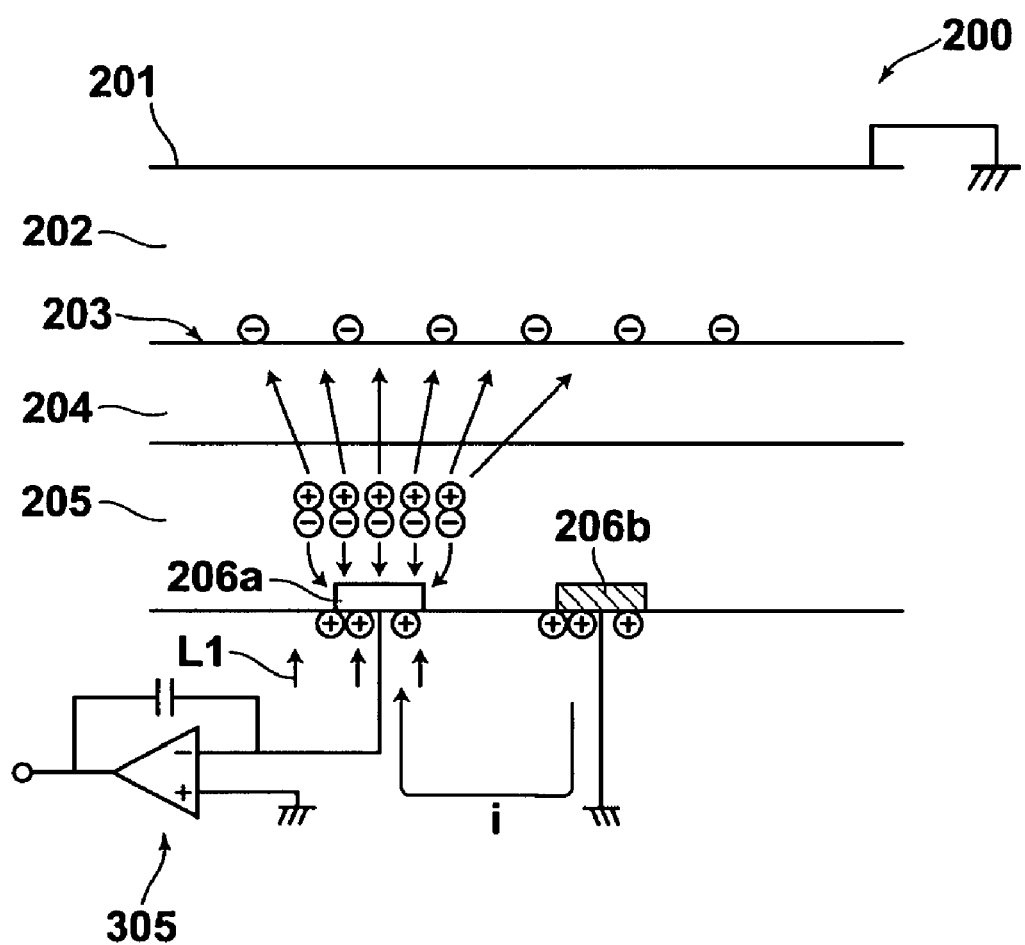
FIG. 23 illustrates a reading operation for reading out a radiation image from the periodic information imaging radiation image detector of the second embodiment of the present invention.

Then, with the first electrode layer 201 being grounded, readout light L1 is irradiated from the side of second linear electrode layer 206, as illustrated in FIG. 23. Readout light L1 transmits through transparent linear electrodes 206a and reaches readout photoconductive layer 205. Positive charges generated by the readout light L1 in readout photoconductive layer 205 combine with latent image charges in storage section 203 while negative charges combine with positive charges charged on opaque linear electrode 206b through charge amplifier 305 connected to opaque linear electrode 206b.

Current flows through charge amplifier 305 when the negative charges generated in readout photoconductive layer 205 are combined with the positive charges charged on opaque linear electrode 206b, and the current is integrated and detected as an image signal.

At this time, charges, flowed out from the first linear electrode group of first linear electrode pair 211 and third linear electrode pair 213 shown in FIG. 21, are detected by charge amplifier 305 as an image signal corresponding to a first phase component. In the mean time, charges, flowed out from the second linear electrode group of second linear electrode pair 212 and fourth linear electrode pair 214 shown in FIG. 21, are detected by charge amplifier 305 as an image signal corresponding to a second phase component.

Thereafter, periodic information imaging radiation image detector 200 or diffraction grating 30 is shifted by shifting mechanism 55 in a direction perpendicular to Y direction, and the image recording in detector 200 and image signal reading from detector 200 are performed at each predetermined position, whereby image signals corresponding to the first and second phase components are detected at each predetermined position.

Then, slit member 12, diffraction grating 30, and periodic information imaging radiation image detector 200 are integrally shifted by a predetermined distance in Y direction by shifting mechanism 55 and the operation identical to that described above is repeated at the position.

Image signals detected in the manner as described above are inputted to phase image acquisition unit 6. Then, phase image acquisition unit 6 generates a phase image based on image signals of a plurality of phase components. More specifically, a partial phase image is generated based on image signals of a plurality of phase components obtained when slit member 12, diffraction grating 30, and periodic information imaging radiation image detector 200 are at a predetermined position in Y direction. Then, a complete phase image is generated by combining partial images obtained at respect positions in Y direction.

In the radiation phase contrast imaging apparatus of the second embodiment, image signals corresponding to six types of phase components may be obtained by shifting periodic information imaging radiation image detector 200 or diffraction grating 30 by shifting mechanism 55 by ⅓ of pitch $P_2$ in a direction perpendicular to Y direction along the plane thereof and taking a radiation image at each position.

In the second embodiment, as in the first embodiment, a pair of linear electrode groups, each having linear electrodes arranged in order may be disposed at different positions so as to have a phase difference between them. This allows image signals of sufficient number of phase components for forming a phase image to be obtained at the same time without performing the shifting by the shifting mechanism described above.

In the radiation phase contrast imaging apparatus of second embodiment, as periodic information imaging radiation image detector 200, a detector to which a negative voltage is applied when recording a radiation image is used. Alternatively, an optical readout type radiation image detector to which a positive voltage is applied when recording a radiation image may be used.

In the radiation phase contrast imaging apparatus according to the first or second embodiment, diffraction grating 30 and periodic information imaging radiation image detector 40/200 are integrally shifted by shifting mechanism 55 along Y direction and stopped at a predetermined position, and then, at the position, diffraction grating 30 or periodic information imaging radiation image detector 40/200 is shifted in a direction perpendicular to Y direction along the plane thereof. If the periodic information imaging radiation image detector is configured to obtain image signals of sufficient types of phase components by one operation, image acquisition may be performed by shifting the detector in Y direction without stopping tentatively.

Figure 24:
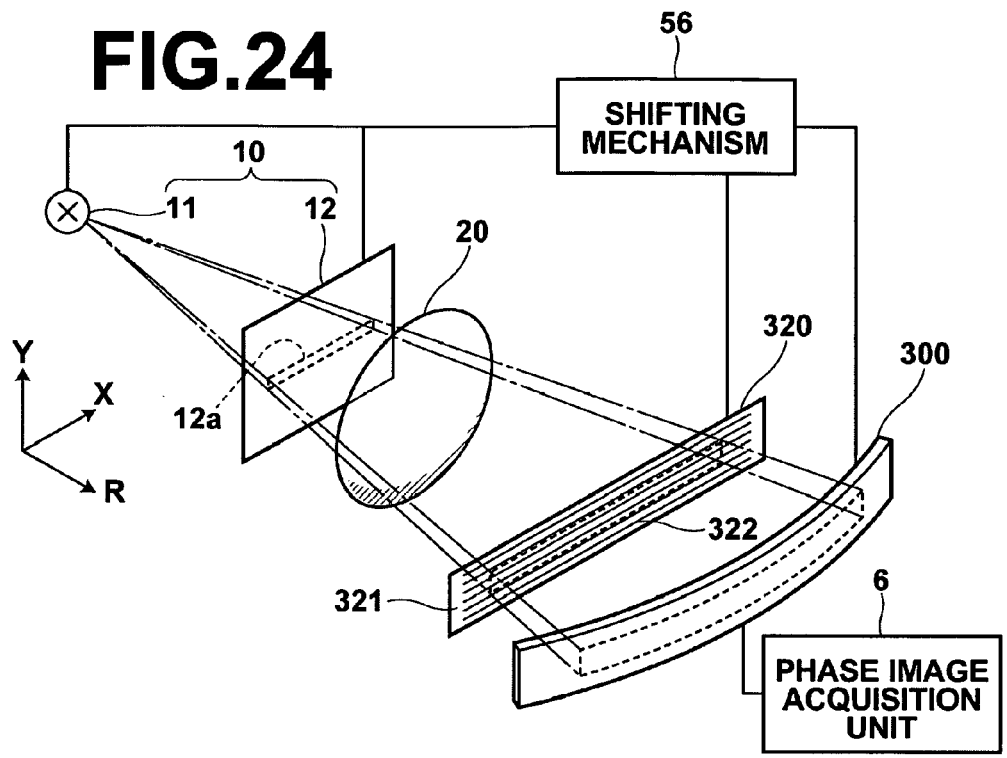
FIG. 24 is a schematic configuration diagram of a third embodiment of the radiation phase contrast imaging apparatus of the present invention.
Figure 25:
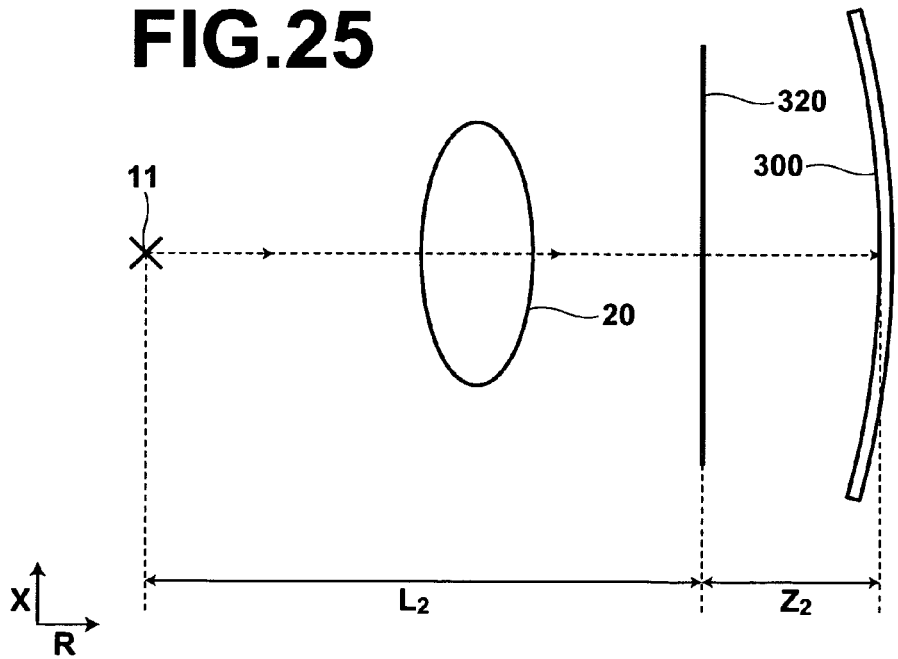
FIG. 25 is an X-R cross-sectional view of the radiation phase contrast imaging apparatus shown in FIG. 24.

Next, a third embodiment of the radiation phase contrast imaging apparatus of the present invention will be described. FIG. 24 is a perspective view of the radiation phase contrast imaging apparatus according to the third embodiment, illustrating the schematic configuration thereof. FIG. 25 is a top view (X-R cross-section) of the radiation phase contrast imaging apparatus shown in FIG. 24. The thickness direction in FIG. 25 corresponds to Y direction in FIG. 24.

As illustrated in FIG. 24, the radiation phase contrast imaging apparatus of the present embodiment includes radiation emission unit 10 for emitting radiation onto subject 20, diffraction grating 320 for receiving radiation transmitted through subject 20 and diffracting the radiation, periodic information imaging radiation image detector 300 for detecting periodic information of the radiation diffracted by diffraction grating 320, phase image acquisition unit 6 for forming a phase image based on an image signal detected by periodic information imaging radiation image detector 300, and shifting mechanism 56 for shifting radiation source 11 and slit member 12 in radiation emission unit 10, diffraction grating 320, and periodic information imaging radiation image detector 300 along Y direction.

The configuration of radiation emission unit 10 is identical to that of radiation emission unit 10 of the first embodiment described above.

As shown in FIG. 26, diffraction grating 320 includes substrate 321 and a plurality of diffraction members 322 provided on substrate 321. Each of the plurality of diffraction members 322 is formed in a linear shape extending in one direction (thickness direction in FIG. 26). The arrangement pitch $P_3$ of the plurality of diffraction members 322 (period of the diffraction grating) is constant in the present embodiment.

Diffraction grating 320 of the present embodiment differs from diffraction grating 30 in extending direction of diffraction members. Diffraction grating 320 is disposed such that the extending direction of diffraction members 322 thereof is parallel to the fan surface of the fan beam having a larger spread angle (fan surface extending along X-R surface in FIG. 1). That is, diffraction grating 320 is disposed such that the extending direction of diffraction members 322 is parallel to X direction in FIG. 1.

The material and thickness of diffraction grating 320 are identical to those of diffraction grating 30 of the first embodiment.

If a radiation emission unit having a plurality of radiation focuses is used as radiation emission unit 10, it is preferable that the apparatus is configured such that an interval $P_0$ between focuses in Y direction, a distance $L_2$ (FIG. 25) from the focus to diffraction grating 320, a distance $Z_2$ (FIG. 25) from diffraction grating 320 to periodic information imaging radiation image detector 300, and an interval $P_2$ (FIG. 10) between linear electrodes of periodic information imaging radiation image detector 300 satisfy Formula (4) below.

$$P_0 = P_2 \times \frac{L_2}{Z_2} \tag{4}$$

In order to make the structure of the radiation phase contrast imaging apparatus of the present embodiment function as a Talbot interferometer, several other conditions need to be substantially satisfied, which will be described hereinafter.

In order to make use of Talbot interference, the distance $Z_2$ between diffraction grating 320 and periodic information imaging radiation image detector 300 needs to substantially satisfy the following condition, if diffraction grating 320 is a phase modulation grating that gives a phase modulation of 90°.

$$Z_2 = \left(m + \frac{1}{2}\right)\frac{P_3^2}{\lambda} \tag{5}$$

where, λ is the wavelength of radiation (normally, center wavelength), m is 0 or a positive integer, $P_3$ is the grating pitch of the diffraction members 322 described above.

Further, the distance $Z_2$ must substantially satisfy the condition below if diffraction grating 320 is a phase modulation grating that gives a phase modulation of 180° or an amplitude modulation grating.

$$Z_2 = (m+1)\frac{P_3^2}{\lambda} \tag{6}$$

Diffraction grating 320 of the present embodiment has a size corresponding to the emission range of a fan beam emitted from radiation emission unit 10 and transmitted through subject 20, and formed in a strip-like shape having a width in X direction larger than that in Y direction.

As shown in FIG. 4, shifting mechanism 56 is a mechanism for integrally shifting radiation source 11, slit member 12, diffraction grating 320, and periodic information imaging radiation image detector 300 along Y direction. This shifting operation by shifting mechanism 56 causes subject 20 to be scanned with the fan beam outputted from radiation emission unit 10 in Y direction.

In the present embodiment, slit member 12, diffraction grating 320, and periodic information imaging radiation image detector 300 are shifted along Y direction as described above, but as in the first embodiment, they may be integrally shifted along an arc with straight line 1 connecting between radiation source 11 and periodic information imaging radiation image detector 300 as the radius centered on radiation source 11, as shown in FIG. 5.

Periodic information imaging radiation image detector 300 is similar to periodic information imaging radiation image detector 40 or 200 according to the first or second embodiment other than that detector 300 is configured such that the extending direction of the linear electrodes thereof is parallel to the fan surface of the fan beam having a larger spread angle (fan surface extending along X-R surface in FIG. 1). Note that periodic information imaging radiation image detector 300 may be formed on a planar surface parallel to diffraction grating 320 in the present embodiment.

Shifting mechanism 56 is a mechanism for integrally shifting diffraction grating 320 and periodic information imaging radiation image detector 300 along Y direction as described above. It is also a mechanism for further shifting, when diffraction grating 320 and periodic information imaging radiation image detector 300 are at a given position in Y direction, diffraction grating 320 or periodic information imaging radiation image detector 300 in Y direction along the surface thereof from the position at a predetermined pitch. For example, diffraction grating 320 or periodic information imaging radiation image detector 300 may be shifted by 1/n (n is an integer not less than two) of the arrangement pitch $P_2$ of the linear electrodes of periodic information imaging radiation image detector 300 and take a radiation image at each position, whereby image signals of n-types of phase components may be obtained. It is preferable, for example, to shift periodic information imaging radiation image detector 300 such that image signals corresponding to four or six types of phase components are obtained. When the charge collection electrode is formed of first linear electrode group 81*a* and second linear electrode group 81*b*, as in the first embodiment, four types of phase components may be obtained by shifting detector 300 by ½ of the arrangement pitch $P_2$ and six types of phase components may be obtained by shifting detector 40 by ⅓ of the arrangement pitch $P_2$. In the present embodiment, even when the periodic information imaging radiation image detector or diffraction grating is formed on a planar surface, diffraction grating 320 or periodic information imaging radiation image detector 300 may be further shifted in Y direction from a given position in Y direction at a predetermined pitch.

The operation for recording a radiation image to and reading out from the periodic information imaging radiation image detector of the radiation phase contrast imaging apparatus according to the third embodiment is similar to that of the first embodiment other than the shifting of periodic information imaging radiation image detector 300 or diffraction grating 320 in Y direction at a predetermined pitch by shifting mechanism 56.

In the radiation phase contrast imaging apparatus of the third embodiment, as periodic information imaging radiation image detector 300 or diffraction grating 320 is shifted by shifting mechanism 56 at a predetermined pitch in Y direction, image recording in detector 300 and image signal reading from detector 300 are performed at each predetermined position, whereby image signals corresponding to the first and second phase components are detected at each predetermined position.

Then, slit member 12, diffraction grating 320, and periodic information imaging radiation image detector 300 are integrally shifted by a predetermined distance in Y direction by shifting mechanism 56 and the operation identical to that described above is repeated at the position.

Image signals detected in the manner as described above are inputted to phase image acquisition unit 6. Then, phase image acquisition unit 6 generates a phase image based on image signals of a plurality of phase components. More specifically, a partial phase image is generated based on image signals of a plurality of phase components obtained when slit member 12, diffraction grating 320, and periodic information imaging radiation image detector 300 are at a predetermined position in Y direction. Then, a complete phase image is generated by combining partial images obtained at respect positions in Y direction.

In the radiation phase contrast imaging apparatus of the third embodiment, it is preferable that the fan beam emitted from radiation emission unit 10 is incident on diffraction grating 320 and periodic information imaging radiation image detector 300 at an angle that substantially does not influence interference conditions of diffraction grating 320 and linear electrodes of periodic information imaging radiation image detector 300 in peripheral portions of exposure areas in Y direction at the positions of diffraction grating 320 and periodic information imaging radiation image detector 300. Hereinafter, such angle will be discussed. Here, the allowable range of the angle will be discussed in terms of the positional displacement of diffraction grating 320.

Assuming a required pitch of diffraction members at a position (r, x) away from intersection point Q between central axis C of the fan beam outputted from radiation emission unit 10 in Y direction and diffraction grating 320 to be Δy, Δy can be represented by Formula (7) below (FIG. 27, which is a Y-R cross-section view of the radiation phase contrast imaging apparatus shown in FIG. 24. The thickness direction in FIG. 27 corresponds to X direction in FIG. 24).

$$\Delta y = r\Delta\theta \times \frac{\tan\theta}{\theta} \times \sqrt{(r^2+y^2)} \times \frac{1}{r} \times \frac{1}{\cos\theta} \quad (7)$$

where, r is the distance from radiation source 11 to diffraction grating 320, and rΔθ is the pitch of diffraction members at intersection point Q between the central axis C of the fan beam and diffraction grating 320.

Here, y/r=tan θ, which is substituted to Formula (7) above, then Δy can be represented by Formula (8) below.

$$\Delta y = r\Delta\theta \times \frac{\tan\theta}{\theta} \times \frac{\sqrt{1+\tan^2\theta}}{\cos\theta} = r\Delta\theta \times \frac{\tan\theta}{\theta\cos^2\theta} \quad (8)$$

Thus, the ratio between the pitch at (r, y) and the pitch rΔθ at intersection point Q can be represented by Formula (9) below.

$$\frac{\Delta y}{r\Delta\theta} = \frac{\tan\theta}{\theta\cos^2\theta} \quad (9)$$

Relationship between θ and Δx/rΔθ obtained based on Formula (9) above is summarized in Table 1 below.

TABLE 1

| | θ | | | | |
|---|---|---|---|---|---|
| | 1.0° | 2.0° | 5.0° | 10.0° | 15.0° |
| Δy/rΔθ | 1.0004 | 1.002 | 1.01 | 1.04 | 1.10 |

Here, if an assumption is made that the pitch $P_3$ of diffraction members 322 of diffraction grating 320 to be 0.8 µm, the width of each diffraction member 322 to be 3 µm, and the width of one pixel of periodic information imaging radiation image detector 300 to be about 120 µm, a phase shift of diffraction grating 320 about 1/12 of the pitch is thought to be undesirable because a signal of different phase component is mixed in the same pixel. Given that the fan beam spreads from the central axis C to Y direction (direction perpendicular to the diffraction members), it is preferable that the positional displacement of diffraction members within one pixel is limited to $8/12 \times 1/2 = 8/24 = 0.333$ µm or less.

If the pitch of the diffraction members on central axis C is 8 µm, the distance between the centers of diffraction members at each end in one pixel at a peripheral portion of the fan beam in Y direction is Δy/rΔθ×8×4.

Accordingly, if Δy/rΔθ×8×4−32<0.333, the condition described above is met.

Thus, Δy/rΔθ<1.010.

Accordingly, it is known from Table 1 above that one side spread angle θ of the fan beam in Y direction needs to be limited to 5° or less. That is, it is preferable that the spread angle of the fan beam in Y direction is limited to 10° or less.

So far the discussion has been made of a case in which the width of one pixel of periodic information imaging radiation image detector 300 is about 120 µm. A discussion will now be made of a case in which the width of one pixel of periodic information imaging radiation image detector 300 is about 80 µm. Note that the pitch and width of the diffraction members are identical to those described above.

In this case, a phase shift of diffraction grating 320 about 1/8 of the pitch is thought to be undesirable because a signal of different phase component is mixed in the same pixel. Given that the fan beam spreads from the central axis C to Y direction (direction perpendicular to the diffraction members), it is preferable that the positional displacement of diffraction members within one pixel is limited to $8/8 \times 1/2 = 8/16 = 0.5$ µm or less.

If the pitch of the diffraction members on central axis C is 8 µm, the distance between the centers of diffraction members at each end in one pixel at a peripheral portion of the fan beam in Y direction is Δy/rΔθ×8×4.

Accordingly, if Δy/rΔθ×8×4−32<0.5, the condition described above is met.

Thus, Δy/rΔθ<1.016.

Accordingly, it is known from Table 1 above that one side spread angle θ of the fan beam in Y direction needs to be limited to 6° or less. That is, it is preferable that the spread angle of the fan beam in Y direction is limited to 12° or less.

The above discussion demonstrates that the pitch of the diffraction members does not depend on the restrictions of spread angle θ of the fan beam.

In the first to third embodiments described above, diffraction grating 30 and periodic information imaging radiation image detector 40/200/300 are formed in strip shapes and they are shifted according to the scanning of the fan beam. But diffraction grating 30 and periodic information imaging radiation image detector 40/200/300 may be formed in a size that covers the entire scanning range of the fan beam. In this case, only slit member 12 may be shifted by the shifting mechanism.

Figure 28:
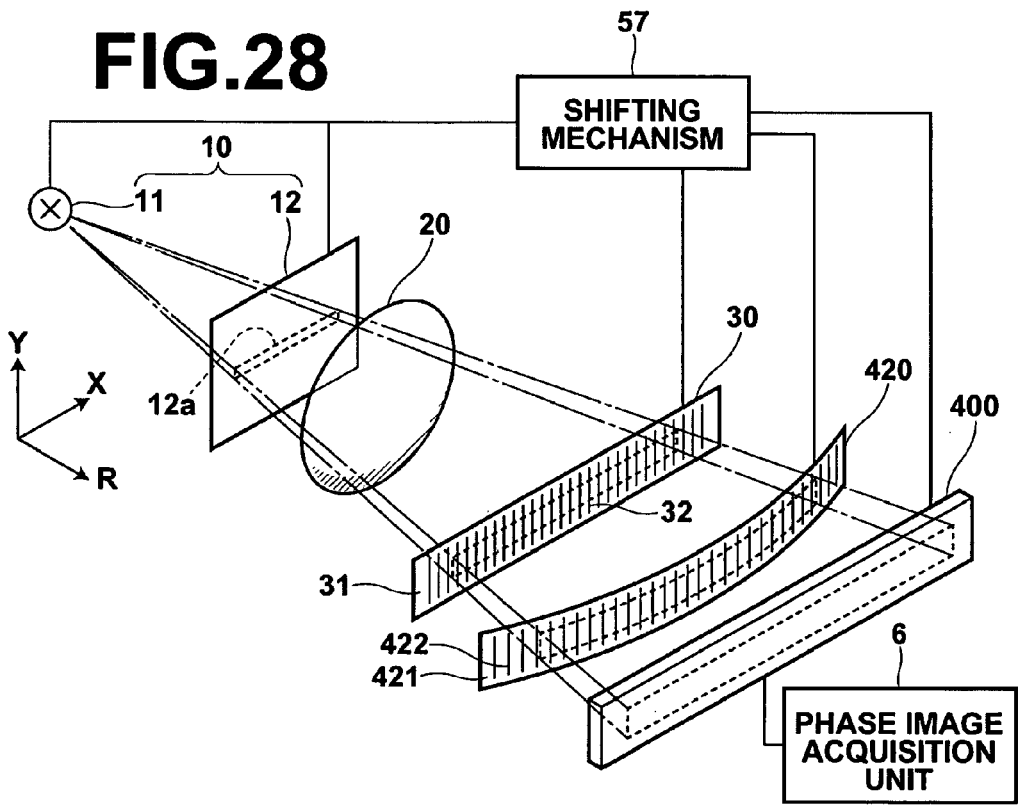
FIG. 28 is a schematic configuration diagram of a fourth embodiment of the radiation phase contrast imaging apparatus of the present invention.
Figure 29:
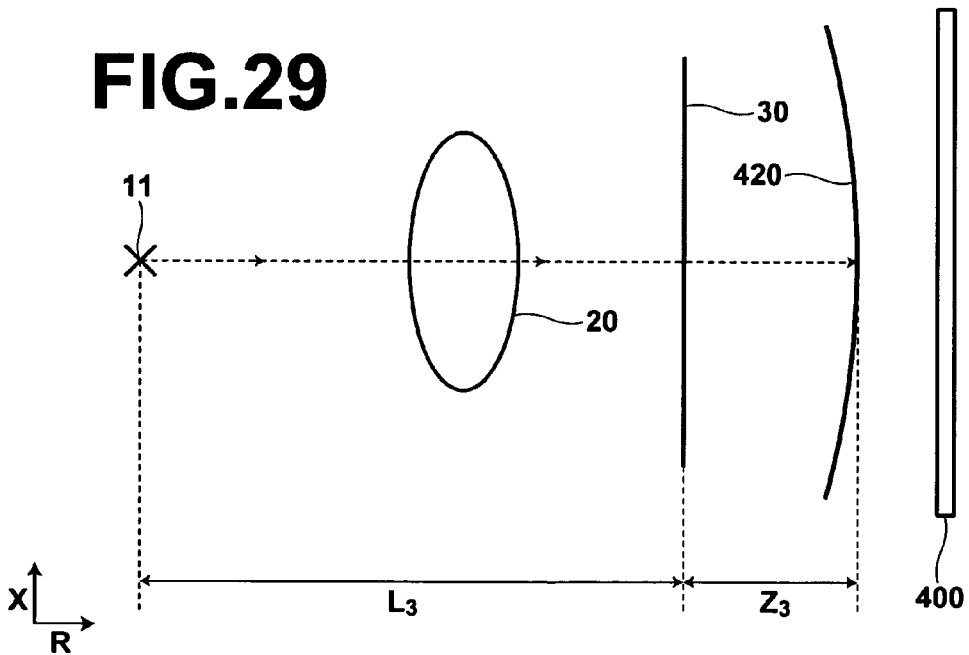
FIG. 29 is an X-R cross-sectional view of the radiation phase contrast imaging apparatus shown in FIG. 28.

Next, a fourth embodiment of the radiation phase contrast imaging apparatus of the present invention will be described. FIG. 28 is a perspective view of the radiation phase contrast imaging apparatus according to the fourth embodiment, illustrating the schematic configuration thereof. FIG. 29 is a top view (X-R cross-section) of the radiation phase contrast imaging apparatus shown in FIG. 28. The thickness direction in FIG. 29 corresponds to Y direction in FIG. 28.

As illustrated in FIG. 28, the radiation phase contrast imaging apparatus of the present embodiment includes radiation emission unit 10 for emitting radiation onto subject 20, first diffraction grating 30 for receiving radiation transmitted through subject 20 and diffracting the radiation, second diffraction grating 420 for diffracting radiation diffracted by first diffraction grating 30, radiation image detector 400 for detecting radiation diffracted by second diffraction grating 420, phase image acquisition unit 6 for forming a phase image based on an image signal detected by radiation image detector 400, and shifting mechanism 57 for shifting slit member 12 in radiation emission unit 10, first diffraction grating 30, second diffraction grating 420, and radiation image detector 400 along Y direction.

The configuration of radiation emission unit 10 is identical to that of radiation emission unit 10 of the radiation phase contrast imaging apparatus of the first embodiment described above. Further, the configuration of first diffraction grating 30 is identical to that of diffraction grating 30 of the radiation phase contrast imaging apparatus of the first embodiment. Note that first diffraction grating 30 may be formed on a cylindrical surface concentric with that of second diffraction grating 420. In this case, the pitch of diffraction grating projected from radiation source 11 to the cylindrical surface needs to be uniform.

Figure 30:
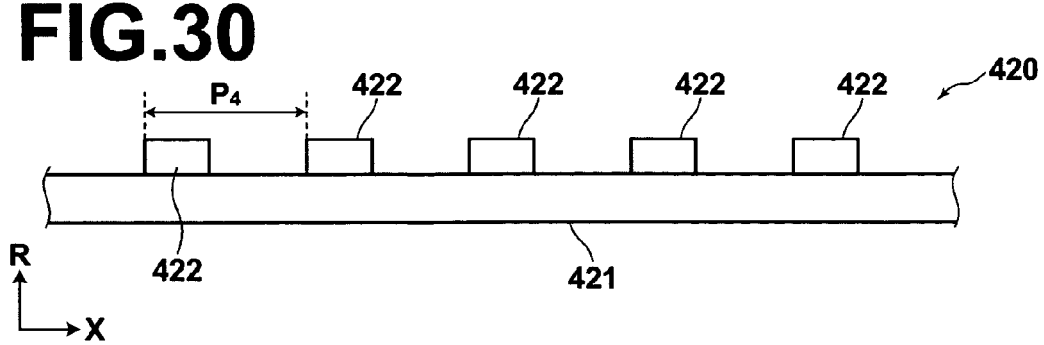
FIG. 30 is a schematic configuration diagram of a second diffraction grating.

As illustrated in FIG. 30, second diffraction grating 420 includes substrate 421 and a plurality of diffraction members 422 provided on substrate 421. Each of the plurality of diffraction members 422 is formed in a linear shape extending in one direction (thickness direction in FIG. 30). The arrangement pitch $P_4$ of the plurality of diffraction members 422 (period of the diffraction grating) is constant in the present embodiment. As for the material of the plurality of diffraction members 422, for example, gold may be used. Preferably, second diffraction grating 420 is an amplitude diffraction grating having diffraction members 422 thicker than those of first diffraction grating 30. In this case, diffraction member 422 needs to have a thickness which is thick enough to sufficiently absorb radiation. For example, the thickness of gold required in the X-ray energy range of ordinary medical diagnosis, in this case, is about ten to several tens of micrometers.

First diffraction grating 30 and second diffraction grating 420 are disposed such that the extending direction of the respective diffraction members is perpendicular to the fan surface of the fan beam having a larger spread angle (fan surface extending along X-R surface in FIG. 1). That is, they are disposed such that the extending direction of diffraction members 422 is parallel to Y direction in FIG. 28.

If a radiation emission unit having a plurality of radiation focuses is used as radiation emission unit 10, it is preferable that the apparatus is configured such that an interval $P_0$ between focuses in X direction, a distance $L_3$ (FIG. 29) from the focus to first diffraction grating 30, a distance $Z_3$ (FIG. 29) from first diffraction grating 30 to second diffraction grating 420, and an interval $P_4$ (FIG. 30) between diffraction members 422 of second diffraction grating 420 satisfy Formula (10) below.

$$P_0 = P_4 \times \frac{L_3}{Z_3} \quad (10)$$

In order to make the structure of the radiation phase contrast imaging apparatus of the present embodiment function as a Talbot interferometer, several other conditions need to be substantially satisfied, which will be described hereinafter.

The distance $Z_3$ from first diffraction grating 30 to second diffraction grating 420 needs to substantially satisfy the following condition, if first diffraction grating 30 is a phase modulation grating that gives a phase modulation of 90°.

$$Z_3 = \left(m + \frac{1}{2}\right)\frac{P_1^2}{\lambda} \quad (11)$$

where, $\lambda$ is the wavelength of radiation (normally, center wavelength), m is 0 or a positive integer, $P_1$ is the grating pitch of the diffraction members 32 described above.

Further, the distance $Z_3$ must substantially satisfy the condition below if diffraction grating 30 is a phase modulation grating that gives a phase modulation of 180° or an amplitude modulation grating.

$$Z_3 = (m + 1)\frac{P_1^2}{\lambda} \quad (12)$$

Second diffraction grating 420 of the present embodiment is faulted along a cylindrical surface with a cylinder axis passing through radiation source 11 and parallel to diffraction members 422 of second diffraction grating 420.

Figure 31:
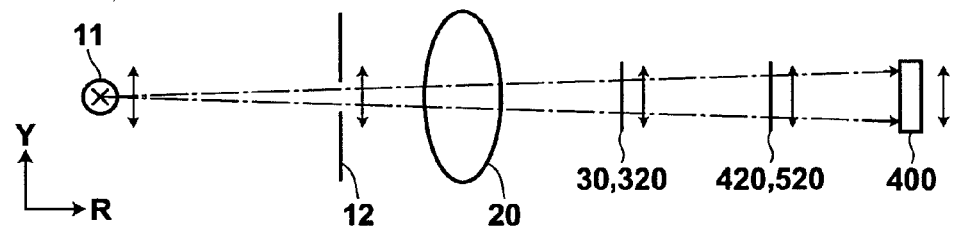
FIG. 31 illustrates an operation of a shifting mechanism.

As illustrated in FIG. 31, shifting mechanism 57 is a mechanism for integrally shifting radiation source 11, slit member 12, first diffraction grating 30, second diffraction grating 420, and radiation image detector 400 along Y direction. This shifting operation by shifting mechanism 57 causes subject 20 to be scanned with the fan beam outputted from radiation emission unit 10 in Y direction.

Figure 32:
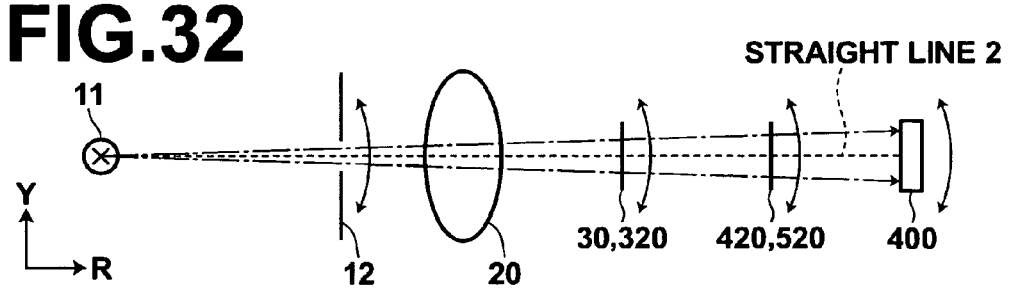
FIG. 32 illustrates an alternative operation of the shifting mechanism.

In the present embodiment, slit member 12, first diffraction grating 30, second diffraction grating 420, and radiation image detector 400 are shifted along Y direction as described above, but they may be integrally shifted along an arc with straight line 2 connecting between radiation source 11 and radiation image detector 400 as the radius centered on radiation source 11, as shown in FIG. 32.

Radiation image detector 400 is a detector that detects a self-image of first diffraction grating 30 formed by radiation incident on first diffraction grating 30 as an image signal intensity modulated by second diffraction grating 420. As for radiation image detector 400, detectors used in conventional radiation phase contrast imaging apparatuses, such as direct conversion or indirect conversion flat panel detectors, imaging plates, intensifying screen-film combinations, and the like may be used. Therefore, it will not be elaborated upon further here.

Shifting mechanism 57 is a mechanism for integrally shifting slit member 12, first diffraction grating 30, second diffraction grating 420, and radiation image detector 400 along Y direction as described above. It is also a mechanism for shifting, when first diffraction grating 30 and second diffraction grating 420 are at a given position in Y direction, first diffraction grating 30 or second diffraction grating 420 in a direction perpendicular to Y direction along the surface thereof from the position. For example, first diffraction grating 30 or second diffraction grating 420 may be shifted by 1/n (n is an integer not less than two) of the arrangement pitch $P_4$ of diffraction members 422 of second diffraction grating 420 and take a radiation image at each position, whereby image signals of n-types of phase components may be obtained. From the n types of image signals, the amount of differential phase shift with respect to each pixel, that is, an amount corresponding to a diffraction angle of radiation caused by subject 20 may be restored, which may be provided as a so-called phase contrast image through various types of image processing and representations. It is preferable, for example, to shift second diffraction grating 420 such that image signals corresponding to four or six types of phase components are obtained.

Next, an operation of the radiation phase contrast imaging apparatus according to the fourth embodiment for recording a radiation image to and reading out from the radiation image detector will be described.

First, subject 20 is placed between radiation emission unit 10 and first diffraction grating 30 (FIG. 28). In the radiation phase contrast imaging apparatus according to the present embodiment, subject 20 is placed between radiation emission unit 10 and first diffraction grating 30, but subject 20 may be placed between first diffraction grating 30 and second diffraction grating 420. In this case, the distance from the subject to periodic information imaging radiation image detector 40 becomes shorter and the magnification ratio is reduced, which allows the apparatus to be easily installed in an existing radiography room.

Next, radiation is outputted from radiation source 11 of radiation emission unit 10 and emitted onto subject 20 after turning into a fan beam by passing through slit 12a of slit member 12. Radiation transmitted through subject 20 is emitted onto first diffraction grating 30. The radiation emitted onto first diffraction grating 30 is diffracted thereby and a self-image of first diffraction grating 30 is formed at a predetermined distance from first diffraction grating 30 in the optical axis direction of the radiation.

For example, when first diffraction grating 30 is a phase modulation grating that gives a phase modulation of 90°, a self-image of first diffraction grating 30 is formed at a distance given by Formula (11) above (Formula (12) above, if first diffraction grating 30 is a phase modulation grating that gives a phase modulation of 180° or an amplitude modulation grating). Here, the wavefront of radiation incident on first diffraction grating 30 is distorted by subject 20 so that the self-image of first diffraction grating 30 is deformed accordingly.

Then, the radiation passes through second diffraction grating 420. As a result, the deformed self-image of first diffraction grating 30 is subjected to intensity modulation through superimposition with second diffraction grating 420, and detected by radiation image detector 400 as an image signal reflecting the wave front distortion.

Then, second diffraction grating 420 is shifted by shifting mechanism 57 in a direction perpendicular to Y direction by 1/n (n is an integer not less than two) of pitch $P_4$ of diffraction members 422, and image signals corresponding to "n" types of phase components, each reflecting the wavefront distortion with respect to each "n", are detected by radiation image detector 400.

Next, radiation source 11, slit member 12, first diffraction grating 30, second diffraction grating 420, and radiation image detector 400 are integrally shifted by a predetermined distance in Y direction by shifting mechanism 57 and the operation identical to that described above is repeated at the position.

Image signals detected in the manner as described above are inputted to phase image acquisition unit 6. Then, phase image acquisition unit 6 generates a phase image based on image signals of a plurality of phase components. More specifically, a partial phase image is generated based on image signals of a plurality of phase components obtained when slit member 12, first diffraction grating 30, second diffraction grating 420, and radiation image detector 400 are at a predetermined position in Y direction. Then, a complete phase image is generated by combining partial images obtained at respect positions in Y direction. Note that, as an alternative method, image signals for a complete phase image with respect to each phase component may be generated first and then an overall phase image may be generated based on the image signals with respect to each phase component. But the method in the present embodiment is preferable because the method is less influenced by the nonuniformity of the gratings and detector.

In the radiation phase contrast imaging apparatus of the fourth embodiment, second diffraction grating 420 is formed along a cylindrical surface. First diffraction grating 30 may also be formed along a cylindrical surface, as in second diffraction grating 420.

Figure 33:
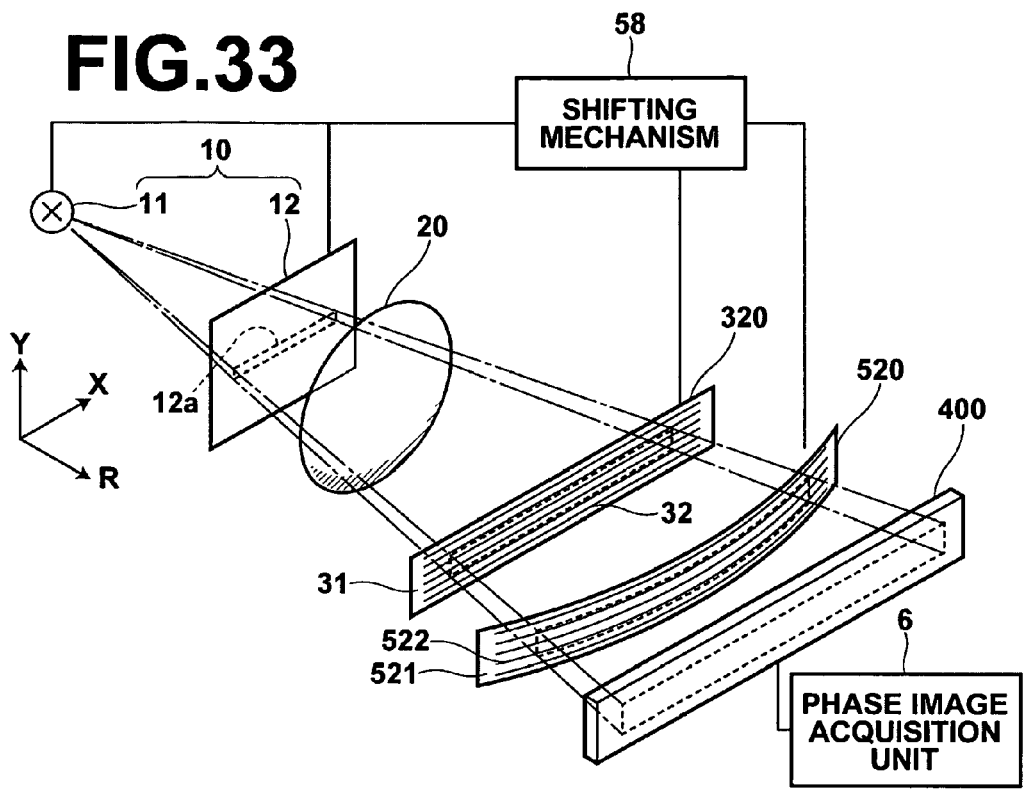
FIG. 33 is a schematic configuration diagram of a fifth embodiment of the radiation phase contrast imaging apparatus of the present invention.
Figure 34:
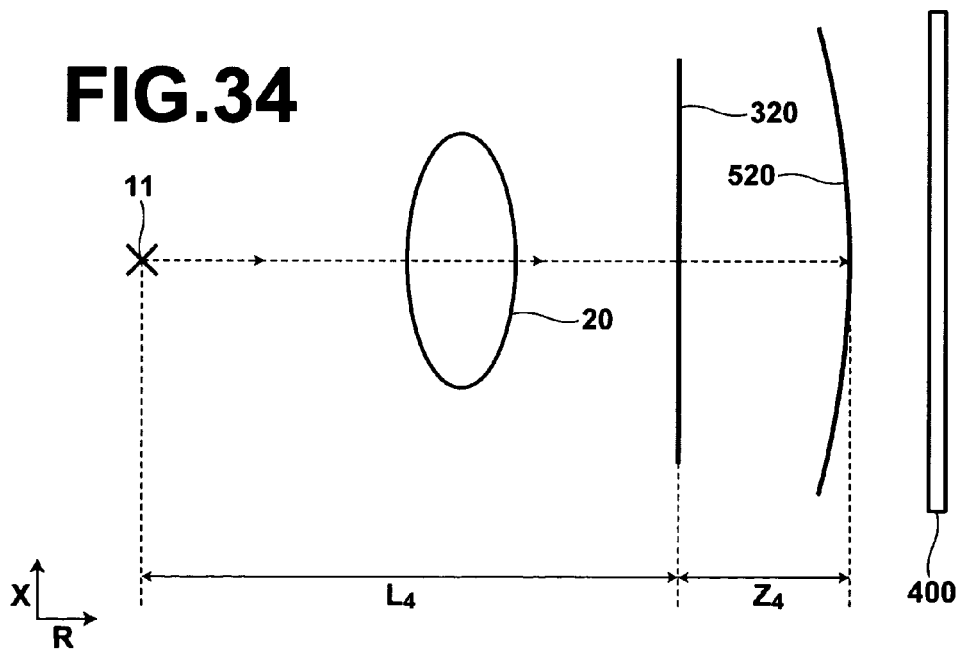
FIG. 34 is an X-R cross-sectional view of the radiation phase contrast imaging apparatus shown in FIG. 33.

Next, a fifth embodiment of the radiation phase contrast imaging apparatus of the present invention will be described. FIG. 33 is a perspective view of the radiation phase contrast imaging apparatus according to the fifth embodiment, illustrating the schematic configuration thereof. FIG. 34 is a top view (X-R cross-section) of the radiation phase contrast imaging apparatus shown in FIG. 33. The thickness direction in FIG. 34 corresponds to Y direction in FIG. 33.

As illustrated in FIG. 33, the radiation phase contrast imaging apparatus of the present embodiment includes radiation emission unit 10 for emitting radiation onto subject 20, first diffraction grating 320 for receiving radiation transmitted through subject 20 and diffracting the radiation, second diffraction grating 520 for diffracting radiation diffracted by first diffraction grating 320, radiation image detector 400 for detecting radiation diffracted by second diffraction grating 520, phase image acquisition unit 6 for forming a phase image based on an image signal detected by radiation image detector 400, and shifting mechanism 58 for shifting radiation source 11 and slit member 12 in radiation emission unit 10, first diffraction grating 320, second diffraction grating 520, and radiation image detector 400 along Y direction.

The configuration of radiation emission unit 10 is identical to that of radiation emission unit 10 of the radiation phase contrast imaging apparatus of the first embodiment described above. Further, the configuration of first diffraction grating 320 is identical to that of diffraction grating 320 of the radiation phase contrast imaging apparatus of the third embodiment.

Figure 35:
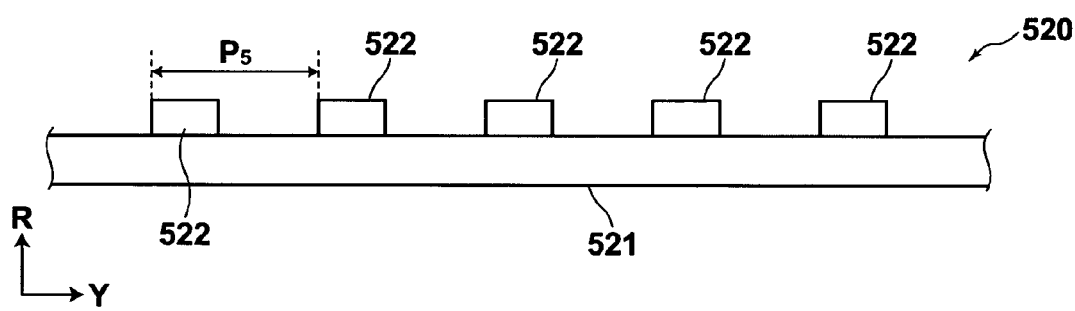
FIG. 35 is a schematic configuration diagram of a second diffraction grating.

As illustrated in FIG. 35, second diffraction grating 520 includes substrate 521 and a plurality of diffraction members 522 provided on substrate 521. Each of the plurality of diffraction members 522 is formed in a linear shape extending in one direction (thickness direction in FIG. 35). The arrangement pitch $P_5$ of the plurality of diffraction members 522 (period of the diffraction grating) is constant in the present embodiment. As for the material of the plurality of diffraction members 522, for example, gold may be used. Preferably, second diffraction grating 520 is an amplitude diffraction grating having diffraction members 522 thicker than those of first diffraction grating 320. In this case, diffraction member 522 needs to have a thickness which is thick enough to sufficiently absorb radiation. For example, the thickness of gold required in the X-ray energy range of ordinary medical diagnosis, in this case, is about ten to several tens of micrometers.

First diffraction grating 320 and second diffraction grating 520 are disposed such that the extending direction of the respective diffraction members is parallel to the fan surface of the fan beam having a larger spread angle (fan surface extending along X-R surface in FIG. 1). That is, they are disposed such that the extending direction of diffraction members 322 and diffraction members 522 is parallel to X direction in FIG. 33.

If a radiation emission unit having a plurality of radiation focuses is used as radiation emission unit 10, it is preferable that the apparatus is configured such that an interval $P_0$ between focuses in Y direction, a distance $L_4$ (FIG. 34) from the focus to first diffraction grating 320, a distance $Z_4$ (FIG. 34) from first diffraction grating 320 to second diffraction grating 520, and an interval $P_5$ (FIG. 35) between diffraction members 522 of second diffraction grating 520 satisfy Formula (13) below.

$$P_0 = P_5 \times \frac{L_4}{Z_4} \tag{13}$$

In order to make the structure of the radiation phase contrast imaging apparatus of the present embodiment function as a Talbot interferometer, several other conditions need to be substantially satisfied, which will be described hereinafter.

The distance $Z_4$ from first diffraction grating 320 to second diffraction grating 520 needs to substantially satisfy the following condition, if first diffraction grating 320 is a phase modulation grating that gives a phase modulation of 90°.

$$Z_4 = \left(m + \frac{1}{2}\right)\frac{P_3^2}{\lambda} \tag{14}$$

where, λ is the wavelength of radiation (normally, center wavelength), m is 0 or a positive integer, $P_3$ is the grating pitch of the diffraction members 322 described above.

The distance $Z_4$ from first diffraction grating 320 to second diffraction grating 520 needs to substantially satisfy the following condition, if first diffraction grating 320 is a phase modulation grating that gives a phase modulation of 180° or an amplitude modulation grating.

$$Z_4 = (m + 1)\frac{P_3^2}{\lambda} \tag{15}$$

Second diffraction grating 520 of the present embodiment is formed along a cylindrical surface with an axis passing through radiation source 11 and parallel to diffraction members 522 of second diffraction grating 520 as the central axis.

As illustrated in FIG. 31, shifting mechanism 58 is a mechanism for integrally shifting, slit member 12, first diffraction grating 320, second diffraction grating 520, and radiation image detector 400 along Y direction. This shifting operation by shifting mechanism 57 causes subject 20 to be scanned with the fan beam outputted from radiation emission unit 10 in Y direction.

In the present embodiment, slit member 12, first diffraction grating 320, second diffraction grating 520, and radiation image detector 400 are shifted along Y direction as described above, but they may be integrally shifted along an arc with straight line 2 connecting between radiation source 11 and radiation image detector 400 as the radius centered on radiation source 11, as shown in FIG. 32.

The configuration of radiation image detector 400 is identical to that of radiation image detector 400 of the fourth embodiment.

Shifting mechanism 58 is a mechanism for integrally shifting slit member 12, first diffraction grating 320, second diffraction grating 520, and radiation image detector 400 along Y direction as described above. It is also a mechanism for further shifting, when first diffraction grating 320 and second diffraction grating 520 are at a given position in Y direction, first diffraction grating 320 or second diffraction grating 520 in Y direction along the surface thereof from the position at a predetermined pitch. For example, first diffraction grating 320 or second diffraction grating 520 may be shifted by 1/n (n is an integer not less than two) of the arrangement pitch $P_5$ of diffraction members 522 of second diffraction grating 520 and take a radiation image at each position, whereby image signals of n-types of phase components may be obtained. It is preferable, for example, to shift second diffraction grating 520 such that image signals corresponding to four or six types of phase components are obtained.

The operation for recording a radiation image to and reading out from the periodic information imaging radiation image detector of the radiation phase contrast imaging apparatus according to the third embodiment is similar to that of the first embodiment other than the shifting of periodic information imaging radiation image detector 300 or diffraction grating 320 in Y direction at a predetermined pitch by shifting mechanism 56.

In the radiation phase contrast imaging apparatus of the fifth embodiment, second diffraction grating 520 is shifted by shifting mechanism 58 in Y direction by 1/n (n is an integer not less than two) of pitch $P_5$ of diffraction members 522, and image signals corresponding to "n" types of phase components, each reflecting the wavefront distortion with respect to each "n", are detected by radiation image detector 400.

Next, radiation source 11, slit member 12, first diffraction grating 320, second diffraction grating 520, and radiation image detector 400 are integrally shifted by a predetermined distance in Y direction by shifting mechanism 58 and the operation identical to that described above is repeated at the position.

Image signals detected in the manner as described above are inputted to phase image acquisition unit 6. Then, phase image acquisition unit 6 generates a phase image based on image signals of a plurality of phase components. More specifically, a partial phase image is generated based on image signals of a plurality of phase components obtained when slit member 12, first diffraction grating 320, second diffraction grating 520, and radiation image detector 400 are at a predetermined position in Y direction. Then, a complete phase image is generated by combining partial images obtained at respect positions in Y direction. In the radiation phase contrast imaging apparatus of the fifth embodiment, second diffraction grating 520 is formed along a cylindrical surface. First diffraction grating 320 may also be formed along a cylindrical surface, as in second diffraction grating 520.

In the radiation phase contrast imaging apparatus of the fifth embodiment, it is preferable that the fan beam emitted from radiation emission unit 10 is incident on first diffraction grating 320 and second diffraction grating 520 at an angle that substantially does not influence interference conditions of first diffraction grating 320 and second diffraction grating 520 in peripheral portions of exposure areas in Y direction at the positions of first diffraction grating 320 and second diffraction grating 520.

Therefore, it is preferable that the spread angle of the fan beam outputted from radiation emission unit 10 in Y direction is not greater than 12° and more preferably not greater than 10°, as discussed in the third embodiment.

In the radiation phase contrast imaging apparatus of the fourth or fifth embodiment, first diffraction grating 30/320, second diffraction grating 420/520, and radiation image detector 400 are formed in strip shapes and they are shifted according to the scanning of the fan beam. But first diffraction grating 30/320, second diffraction grating 420/520, and radiation image detector 400 may be formed in a size that covers the entire scanning range of the fan beam. In this case, only slit member 12 may be shifted by the shifting mechanism.

In the radiation phase contrast imaging apparatuses of the first to fifth embodiments, if a configuration is adopted in which image signals corresponding to a plurality of phase components are obtained, a phase shift differential image (distribution of radiation angles bent by the diffraction effects of the subject) or a phase shift image (integrated phase shift differentials) may be calculated using the image signals, which may also be used according to an intended purpose of the image acquisition. For the calculation method of the phase shift differential image or phase shift image, reference is made to, for example, U.S. Pat. No. 7,180,979.

Further, each of the radiation phase contrast imaging apparatuses of the first to fifth embodiments allows stereoscopic observation of a subject and an internal structure of the subject by obtaining images of the subject in a plurality of different projection directions by rotating or shifting either the subject or radiation phase contrast imaging apparatus and performing arithmetic operation on the obtained images. In this case, unlike a conventional tomography or a tomosynthesis, a stereoscopic image is formed by a refractive index distribution, and a structure which is difficult to be visualized by the sensitivity of the conventional tomography or tomosynthesis may be visualized.

What is claimed is:

1. A radiation phase contrast imaging apparatus, comprising:
 a radiation emission unit that includes a radiation source and outputs a fan beam of radiation;
 a diffraction grating onto which radiation outputted from the radiation emission unit is emitted; and
 a periodic information imaging radiation image detector that includes multiple linear electrodes and detects periodic information of radiation diffracted by the diffraction grating, wherein:
 the radiation emission unit and the periodic information imaging radiation image detector are disposed such that an extending direction of the linear electrodes of the periodic information imaging radiation image detector is perpendicular to a fan surface of the fan beam having a larger spread angle; and
 the radiation emission unit is configured to scan the fan beam in the perpendicular direction.

2. The radiation phase contrast imaging apparatus of claim 1, wherein the periodic information imaging radiation image detector is disposed along a cylindrical surface with a cylinder axis passing through the radiation source and parallel to the extending direction of the linear electrodes.

3. The radiation phase contrast imaging apparatus of claim 1, wherein the periodic information imaging radiation image detector is configured to be shifted in the perpendicular direction according to the scanning of the fan beam.

4. The radiation phase contrast imaging apparatus of claim 1, wherein the periodic information imaging radiation image detector is configured to be shifted along an arc with a straight line connecting between the radiation source and the periodic information imaging radiation image detector as the radius.

5. A radiation phase contrast imaging apparatus, comprising:
 a radiation emission unit that includes a radiation source and outputs a fan beam of radiation;
 a diffraction grating onto which radiation outputted from the radiation emission unit is emitted; and
 a periodic information imaging radiation image detector that includes multiple linear electrodes and detects periodic information of radiation diffracted by the diffraction grating, wherein:
 the radiation emission unit and the periodic information imaging radiation image detector are disposed such that an extending direction of the linear electrodes of the periodic information imaging radiation image detector is parallel to a fan surface of the fan beam having a larger spread angle; and
 the radiation emission unit is configured to scan the fan beam in a direction perpendicular to the fan surface.

6. The radiation phase contrast imaging apparatus of claim 5, wherein the periodic information imaging radiation image detector is disposed on a planar surface or along a cylindrical surface with a cylinder axis passing through the radiation source and parallel to the direction in which the linear electrodes are arrayed.

7. The radiation phase contrast imaging apparatus of claim 5, wherein the periodic information imaging radiation image detector is configured to be shifted in the perpendicular direction according to the scanning of the fan beam.

8. The radiation phase contrast imaging apparatus of claim 5, wherein the periodic information imaging radiation image detector is configured to be shifted along an arc with a straight line connecting between the radiation source and the periodic information imaging radiation image detector as the radius.

9. A radiation phase contrast imaging apparatus, comprising:
 a radiation emission unit that includes a radiation source and outputs a fan beam of radiation;
 a first diffraction grating onto which radiation outputted from the radiation emission unit is emitted;
 a second diffraction grating that diffracts radiation diffracted by the first diffraction grating; and
 a radiation image detector that detects radiation diffracted by the second diffraction grating, wherein:
 the radiation emission unit and the first and second diffraction gratings are disposed such that an extending direction of diffraction members of the first and second diffraction gratings is perpendicular to a fan surface of the fan beam having a larger spread angle;
 the radiation emission unit is configured to scan the fan beam in the perpendicular direction; and
 the second diffraction grating is disposed along a cylindrical surface with a cylinder axis passing through the radiation source and parallel to the extending direction of the diffraction members.

10. The radiation phase contrast imaging apparatus of claim 9, wherein the second diffraction grating is configured to be shifted in the perpendicular direction according to the scanning of the fan beam.

11. A radiation phase contrast imaging apparatus, comprising:
 a radiation emission unit that includes a radiation source and outputs a fan beam of radiation;
 a first diffraction grating onto which radiation outputted from the radiation emission unit is emitted;
 a second diffraction grating that diffracts radiation diffracted by the first diffraction grating; and
 a radiation image detector that detects radiation diffracted by the second diffraction grating, wherein:
 the radiation emission unit and the first and second diffraction gratings are disposed such that an extending direction of diffraction members of the first and second diffraction gratings is perpendicular to a fan surface of the fan beam having a larger spread angle;
 the radiation emission unit is configured to scan the fan beam in the perpendicular direction; and
 the second diffraction grating is configured to be shifted along an arc with a straight line connecting between the radiation source and the second diffraction grating as the radius.

12. A radiation phase contrast imaging apparatus, comprising:
 a radiation emission unit that includes a radiation source and outputs a fan beam of radiation;
 a first diffraction grating onto which radiation outputted from the radiation emission unit is emitted;
 a second diffraction grating that diffracts radiation diffracted by the first diffraction grating; and
 a radiation image detector that detects radiation diffracted by the second diffraction grating, wherein:
 the radiation emission unit and the first and second diffraction gratings are disposed such that an extending direction of diffraction members of the first and second diffraction gratings is parallel to a fan surface of the fan beam having a larger spread angle;
 the radiation emission unit is configured to scan the fan beam in a direction perpendicular to the fan surface; and
 the second diffraction grating is disposed on a planar surface or along a cylindrical surface with a cylinder axis passing through the radiation source and parallel to the direction in which the diffraction members are arrayed.

13. The radiation phase contrast imaging apparatus of claim 12, wherein the second diffraction grating is configured to be shifted in the perpendicular direction according to the scanning of the fan beam.

14. A radiation phase contrast imaging apparatus, comprising:
 a radiation emission unit that includes a radiation source and outputs a fan beam of radiation;
 a first diffraction grating onto which radiation outputted from the radiation emission unit is emitted;
 a second diffraction grating that diffracts radiation diffracted by the first diffraction grating; and
 a radiation image detector that detects radiation diffracted by the second diffraction grating, wherein:
 the radiation emission unit and the first and second diffraction gratings are disposed such that an extending direction of diffraction members of the first and second diffraction gratings is parallel to a fan surface of the fan beam having a larger spread angle;
 the radiation emission unit is configured to scan the fan beam in the perpendicular direction; and the second diffraction grating is configured to be shifted along an arc with a straight line connecting between the radiation source and the second diffraction grating as the radius.

* * * * *